(12) United States Patent
Kim

(10) Patent No.: US 7,282,523 B2
(45) Date of Patent: Oct. 16, 2007

(54) PHARMACEUTICAL COMPOSITIONS USEFUL IN PREVENTION AND TREATMENT OF BETA-AMYLOID PROTEIN-INDUCED DISEASE

(76) Inventor: Darrick S. H. L. Kim, 834 Pinehurst La., Schaumburg, IL (US) 60193

( * ) Notice: Subject to any disclaimer, the term of this patent is extended or adjusted under 35 U.S.C. 154(b) by 165 days.

(21) Appl. No.: 11/084,316

(22) Filed: Mar. 18, 2005

(65) Prior Publication Data
US 2005/0197393 A1 Sep. 8, 2005

Related U.S. Application Data

(63) Continuation of application No. 10/111,039, filed as application No. PCT/US00/41436 on Oct. 23, 2000, now Pat. No. 6,887,898.

(60) Provisional application No. 60/161,145, filed on Oct. 22, 1999.

(30) Foreign Application Priority Data
Oct. 23, 2000  (EP)  ................... 00986827

(51) Int. Cl.
A61K 31/12 (2006.01)
A61K 31/075 (2006.01)
A61K 31/045 (2006.01)
(52) U.S. Cl. .............. 514/675; 514/715; 514/724
(58) Field of Classification Search ........ 514/532, 514/679, 675, 715, 724

See application file for complete search history.

(56) References Cited

U.S. PATENT DOCUMENTS

| 5,089,636 A | 2/1992 | Kwak et al. |
| 5,266,344 A | 11/1993 | Mimura et al. ............. 426/546 |
| 5,587,358 A | 12/1996 | Sukigara et al. |

FOREIGN PATENT DOCUMENTS

| JP | 02-193930 | * 7/1990 |
| JP | 07206669 | 8/1995 |
| JP | 08-040970 | * 2/1996 |
| JP | 11246398 | 9/1999 |
| WO | WO 97/03674 | 2/1997 |
| WO | WO 98/51302 | 11/1998 |
| WO | WO 00/70949 | 11/2000 |

OTHER PUBLICATIONS

Locksley et al, Perkin Transactions1: J. of The Chemical Society, 1972, 23, p. 3001-3006.*
Beard, et al., "Nonsteroidal Anti-Inflammatory Drug Use and Alzheimer's Disease: A Case-Control Study in Rochester, MN 1980-1984," *Mayo Foundation for Medical Education and Research* 73(10), 951-955 (1998).

(Continued)

Primary Examiner—Taylor Victor Oh
(74) Attorney, Agent, or Firm—Marshall, Gerstein & Borun LLP

(57) ABSTRACT

The invention provides methods for treating beta-Amyloid protein-induced disease, pharmaceutical compositions and compounds useful for the same, and the use of these compounds for the manufacture of a medicament for treating the same. More particularly, the invention relates to the use of natural product compounds isolated from turmeric, *gingko biloba*, and ginger, and synthetic chemical analogues thereof, for the treatment of a beta-Amyloid protein-induced disease.

6 Claims, 11 Drawing Sheets

OTHER PUBLICATIONS

Behl et al., "Hydrogen Peroxide Mediates Amyloid β Protein Toxicity," *Cell* 77, 817-827 (1994).

Carr, et al., "Current Concepts in the Pathogenesis of Alzheimer's Disease," *The American Journal of Medicine*, 103(3A), 3S-10S (1997).

Cuajungco, et al., "Zinc Metabolism in the Brain: Relevance to Human Neurodegenerative Disorders," *Neurobiology of Disease* 4, 137-169 (1997).

Davis, et al., "The Amyloid Beta-Protein of Alzheimer's Disease is Chemotactic for Mononuclear Phagocytes," *Biochemical and Biophysical Research Communications* 189(2) 1096-1100 (1992).

Friedlich et al., "Involvement of Free Oxygen Radicals in β-Amyloidosis: An Hypothesis," *Neurobiology of Aging* 15(4), 443-455 (1994).

Ghanta et al., "A Strategy for Designing Inhibitors of β-Amyloid Toxicity," *The Journal of Biological Chemistry* 271(47): 29525-29528 (1996).

Goedert, "Tau protein and the neurofibrillary pathology of Alzheimer's disease," *TINS* 16(11) 460-465 (1993).

Green et al., "Nuclear Estrogen Receptor-Independent Neuroprotection by Estratrienes: A Novel Interaction with Glutathione," *Neuroscience* 84(1), 7-10 (1998).

Haass et al., "Cellular Processing of β-Amyloid Precursor Protein and the Genesis of Amyloid β-Peptide," *Cell* 75 10-39-1042 (1993).

Harkany et al., "Cholinotoxic effects of β-amyloid $_{(1-42)}$ peptide on cortical projections of the rat nucleus *Basalis magnocellularis*," *Brain Research* 695, 71-75 (1995).

Hefti, "Development of Effective Therapy for Alzheimer's Disease Based on Neurotrophic Factors," *Neurobiology of Aging* 15(2), S193-S194 (1994).

Henderson, "The epidemiology of estrogen replacement therapy and Alzheimer's disease," *American Academy of Neurology* 48(5), S. 7, 275-355 (1997).

Hensley et al., "A model for β-amyloid aggregation and neurotoxicity based on free radical generation by the peptide: Relevance to Alzheimer disease," *PNAS USA* 91, 3270-3274 (1994).

Hertel et al., "Inhibition of the electrostatic interaction between β-amyloid peptide and membranes prevents β-amyloid-induced toxicity," *PNAS USA* 94, 9412-9417 (1997).

Hidalgo et al., "Determination of the Carnosic Acid Content in Wild and Cultivated *Rosmarinus officinalis*," *J. Agric. Food. Chem* 46, 2624-2627 (1998).

Hopia et al., "Effect of Different Lipid Systems on Antioxidant Activity of Rosemary Constituents Carnosol and Carnosic Acid with and without α-Tocopherol," *J. Agric. Food Chem* 44, 2030-2036 (1996).

Hoshi et al., "Nontoxic Amyloid β Peptide $_{1-42}$ Suppresses Acetylocholine Synthesis," *The Journal of Biological Chemistry* 272(4), 2038-2041 (1997).

Ihara et al., "Phosphorylated Tau Protein Is Integrated into Paired Helical Filaments in Alzheimer's Disease," *J. Biochem* 99, 1807-1810 (1986).

Jitoe et al., "Antioxidant Activity of Tropical Ginger Extracts and Analysis of the Contained Curcuminoids," *J. Agric. Food Chem* 40, 1337-1340 (1992).

Kiegeris et al., "Activation of Macrophages by Alzheimer β Amyloid Peptide," *Biochemical and Biophysical Research Communications* 199(2), 984-991 (1994).

Kihara et al., "Stimulation of α4β2 nicotinic acetylcholine receptors inhibits β-amyloid toxicity," *Brain Research* 792, 331-334 (1998).

Kikuzaki et al., "Antioxidant Effects of Some Ginger Constituents," *Journal of Food Science* 58(6), 1407-1410 (1993).

Kim et al., "Shogaols from *Zingiber officinale* Protect IMR32 Human Neuroblastoma and Normal Human Umbilical Vein Endothelial Cells from β-Amyloid (25-35) Insult," *Letter . . . Planta Med 2002* 68, 375-376 (2002).

Kumar et al., "The Acute Neurotoxic Effect of β-Amyloid on Mature Cultures of Rat Hippocampal Neurons is Attenuated by the Anti-Oxidant U-78517F," *Intern. J. Neuroscience* 79, 185-190 (1994).

Lahiri et al., "Tacrine Alters the Secretion of the Beta-Amyloid Precursor Protein in Cell Lines," *Journal of Neuroscience Research* 37: 777-787 (1994).

Lorenzo et al., "Amyloid Fibril Toxicity in Alzheimer's Disease and Diabetes$^\alpha$", *Annals New York Academy of Sciences*: 89-95.

Lucca et al., "Influence of cell culture conditions on the protective effect of antioxidants against β-amyloid toxicity: studies with lazaroids," *Brain Research* 764: 2930298 (1997).

Manelli et al., "β-Amyloid-Induced Toxicity in Rat Hippocampal Cells: In Vitro Evidence for the Involvement of Free Radicals," Brain Research Bulletin 18(6): 569-576 (1995).

Mattson, "Neuroprotective Signal Transduction: Relevance to Stroke," *Neurosci Biobehav Rev* 21(2): 193-206 (1997).

Maurice et al., Amnesia induced in mice by centrally administers β-amyloid peptides involves cholinergic dysfunction, *Brain Research* 706:181-193 (1996).

Müller et al. "Protection of Flupertine on β-Amyloid-Induced Apoptosis in Neuronal Cells In Vitro: Prevention of Amyloid-Induced Glutathion Depletion," *Journal of Neurochemistry* 68(6):2371-2377 (1997).

Nakatani et al., "A New Diterpene Lactone, Rosmadial, from Rosemary (*Rosmarinus officinalis* L.)," *Agric. Biol. Chem.* 47(2):353-358 (1983).

Park et al., "Discovery of Natural Products from *Curcuma longa* that Protect Cells from Beta-Amyloid Insult: A Drug Discovery Effort Against Alzheimer's Disease," *Journal of Natural Products* 65(9):1227-1231 (2002).

Parnetti et al., "Cognitive Enhancement Therapy for Alzheimer's Disease," *Drugs* 53(5): 752-768 (1997).

Pasinetti et al., "Cyclooxygenase-2 Expressiosn is Increased in Frontal Cortex of Alzheimer's Disease Brain," *Neuroscience* 87(2):319-3224 (1998).

Pike et al., "Neurodegeneration Induced by β-Amyloid Peptides in vitro: The Role of Peptide Assembly State," *The Journal of Neuroscience* 13(4) 1676-1687 (1993).

Pike et al., "β-Amyloid Neurotoxicity In Vitro: Evidence of Oxidative Stress but Not Protection. by Antioxidants," *Journal of Neurochemistry* 69(4):1601-1611 (1997).

Pollack et al., "Sulfonated dyes attenuate the toxic effects of β-amyloid in a structure-specific fashion," *Neuroscience Letters* 197: 211-214 (1995).

Preston et al., "Toxic effects of β-amyloid(25035) on immortalized rat brain endothelian cell: protection by carnosine, homecarnosine and β-alanine," *Neuroscience Letters* 242: 105-108 (1998).

Puttfarcken et al., "Inhibition of Age-Induced β-Amyloid Neurotoxicity in Rat Hippocampal Cells," *Experimental Neurology* 138: 73-81 (1996).

Seidl et al., "Evidence against increased glycoxidation in patients with Alzheimer's disease," *Neuroscience Letters* 232, 49-52 (1997).

Seiger et al., "Intraracial infusion of purified nerve growth factor to an Alzheimer patient: the first attempt of a possible future treatment strategy," *Behavioral Brain Research* 57:255-261 (1993).

Shastry, "Molecular Genetics of Familial Alzheimer Disease," *The American Journal of the Medical Sciences*, 315(4), 266-272 (1998).

Tatton et al., "Modulation of gene expression rather than monoamine oxidase inhibition: (-)-Deprenyl-related compounds in controlling neurodegeneration," *Neurology* 47(6) S. 3: 1715-1835 (1996).

Thomas et al., "Beta-Amyloid-mediated vasoactivity and vascular endothelial damage," *Nature* 380(6570):168-171 (1996).

Trojanowski et al., "Paired Helical Filament τ in Alzheimer's Disease-The Kinase Connection," *American Journal of Pathology* 144(3) 449-453 (1994).

Trojanowski et al. "Phosphorylation of paired helical filament tau in Alzheimer;s disease neurofibrallary lesions: focusing on phosphates," The FASB Journal 9:1571-1576 (1005).

Yaar et al., "Binding of β-Amyloid to the p75 Neurotrophin Receptor Induces Apoptosis," *The Journal of Clinical Investigation* 100(9): 2333-2340 (1997).

Yan et al., "RAGE and amyloid-β peptide neurotoxicity in Alzheimer's disease," *Nature* 382 (1996).

Zhou et al., "Actions of Neurotoxic β-Amyloid on Calcium Homeostasis and Viability of PC12 Cells are Blocked by Antioxidants but not by Calcium Channel Antagonists," *Journal of Neurochemistry* 67(4): 1419-1425 (1996).

Artico et al., "Geometrically and Conformationally Restrained Cinnamoyl Compounds as Inhibitors of HIV-1 Integrase: Synthesis, Biological Evaluation, and Molecular Modeling," *J. Med. Chem.*, 41:3948-3960 (1998).

Chang et al., "The Effect of Chinese Medicinal Herb *Zingiberis rhizoma* Extract on Cytokine Secretion by Human Peripheral Blood Mononuclear Cells," *J. Ethnopharmacology*, 48:13-19 (1995).

Clostre, "*Ginkgo biloba* extract (EGb 761): A State of Art at the Dawn of the Third Millennium," *Annales Pharmaceutiques Francaises*, 57, no. Suppl. 1:1S8-1S88 (1999).

Conney et al., "Inhibitory Effect of Curcumin and Some Related Dietary Compounds on Tumors Promotion and Arachidonic Acid Metabolism in Mouse Skin," *Advances in Enzyme Regulation*, Proceedings of the Thirty-First Symposium on Regulation of Enzyme Activity and Synthesis in Normal and Neoplastic Tissues held at Indiana University School of Medicine, Weber, ed., vol. 31, pp. 385-396 (1991).

Gellerman et al., "Antimicrobial Effects of Anacardic Acids," *Canadian Journal of Microbiology*, 15:1219-1223 (1969).

He et al., "High-performance Liquid Chromatography-electrospray Mass Spectrometric Analysis of Pungent Constituents of Ginger," *J. Chromatography A*, 796:327-334 (1998).

Hiserodt et al., "Isolation of 6-, 8-, and 10-Gingerol from Ginger Rhizome by HPLC and Preliminary Evaluation of Inhibition of *Mycobacterium avium* and *Mycobacterium tuberculosis,*" *J. Agric. Food Chem.*, 46:2504-2508 (1998).

Huang et al., "Novel Bipheny Ether Liganans from the Rhizomes of *Curcuma chuanyujin,*" *Chem. Pharm. Bull,* 48(8):1228-1229 (2000).

Itokawa et al., "Antitumor Principles from *Ginkgo biloba* L.," *Chem. Pharm. Bull.*, 35(7):3016-3020 (1987).

Jung et al., "Effects of Curcumin on the Microglial Activation," *Yakhak Hoeji*, 44(5):448-454 (2000).

Kelloff et al., "Chemopreventive Drug Development: Persepectives and Progress," *Cancer Epidermiol. Biomarkers & Prev.*, 3:85-98 (1994).

Khopde et al., "Free Radical Scavenging Ability and Antioxidant Efficieny of Curcumin and its Substituted Analogue," *Biophysical Chemistry*, 80:85-91 (1999).

Kim et al., "Inhibition of β-Amyloid Neurotoxicity in PC12 Cells by CLZ-1, CLZ-2 and CLZ-3 Isolated From *Curcuma longa, Zingiberaceae*: An Approach Toward A Rational Drug Discovery Of Anti-Alzheimer Disease," *Society For Neuroscience Abstracts*, 24(1-2):1457 (1998).

Kim et al., "Curcuminoids from *Curcuma longa* L. (*Zingiberaceae*) that Protect PC12 Rat pheochromocytome and Normal Human Umbilical Vein Endothelial Cells from βA(1-42) Insult," *Neuroscience Letters*, 303:57-61 (2001).

Kuner et al., "β-Amyloid Binds to p75$^{NTR}$ and Activates NFκB in Human Neuroblastoma Cells," *J. Neuroscience Res.*, 54:798-804 (1998).

Lee et al., "Induction of Apoptosis in HL-60 Cells by Pungent Vanilloids, [6]-gingerol and [6]-paradol," *Cancer Letters*, 134:163-168 (1998).

Lim et al., "Prevention of LTP deficits in Alzheimer Ttransgenic HuAPPSw Mice Using a Phenolic Anti-oxidant/anti-inflammatory Compound," *Society for Neuroscience Abstracts*, 26(1-2):Abstract No. 763.9 (2000).

Maurer et al., "Clinical Efficacy of *Ginkgo biloba* Special Extract EGb 761 in Dementia of the Alzheimer Type," *J. psychiat. Res.*, 31(6):645-655 (1997).

Morimoto et al., "Sterische Struktur der Giftstoffe aus dem Fruchtfleisch on *Ginkgo biloba* L.", *Chem. Pharm. Bull.*, 16(11):2282-2286 (1968).

Nagabhushan et al., "Mutagenicity Of Gingerol And Shogaol And Antimutagenicity Of Zingerone in *Salmonella*/Microsome Assay," *Cancer Letters*, 36:221-233 (1987).

Nakayama, "Strategy of Chemical Modification to Free Radical Scavengers for Suppression of Hydrogen Peroxide-Induced Cytotoxicity," *Food Factors Cancer Prev., Int. Conf.*, 1995, pp. 642-646 (1997).

Niijima et al., "Effect of Oral Administration of *Pinellia ternata, Zingiberis rhizoma* and Their Mixture on the Efferent Activity of the Gastric Branch of the Vagus Nerve in the Rat," *Neuroscience Letters*, 258:5-8 (1998).

Nurfina et al., "Synthesis of Some Symmetrical Curcumin Derivatives and Their Anti-inflammatory Activity," *Eur. J. Med Chem.*, 32:321-328 (1997).

Osawa et al., "Antioxidative Activity of Tetrahydrocurcuminoids," *Biosci. Biotech. Biochem.*, 59(9):1609-1612 (1995).

Prasain et al., "Inhibitory Effect of Diarylheptanoids on Nitric Oxide Production in Activated Murine Macrophages," *Biol. Pharm. Bull.*, 21(4):371-374 (1998).

Ruby et al., "Anti-tumour and Antioxidant Activity of Natural Curcuminoids," *Cancer Letters*, 94: 79-83 (1995).

Schulick, Ginger, *Common Spice & Wonder Drug*, 3$^{rd}$ edition, Hohm Press, pp. 1-166 (1996).

Skolnick, "Old Chinese Herbal Medicine Used for Fever Yields Possible New Alzheimer Disease Therapy," *JAMA*, 277(10):776 (1997).

Soliman et al., "In vitro Attenuation of Nitric Oxide Production in C6 Astrocyte Cell Culture by Various Dietary Compounds," *Proc. Soc. Exper. Biol. Med.*, 218(4):390-397 (1998).

Suekawa et al., "Pharmacological Studies On Ginger. I. Pharmacological Actions Of Pungent Constituents, (6)-Gingerol and (6)-Shogaol," *J. Pharm Dyn.*, 7:836-848 (1984).

Venkateshwarlu, "Cyclo-Oxygenase Inhibitors From Spices," *Indian Drugs*, 34(8):427-432 (1997).

Yoshikawa et al., "Qualitative and Quantitative Analysis of Bioactive Principles in *Zingiberis rhizoma* by Means of High Performance Liquid Chromatography and Gas Liquid Chromatography. On the Evaluation of *Zingiberis rhizoma* and Chemical Change of Constituents during *Zingiberis rhizoma* Processing," Regular Articles, *Yakugaku Zasshi*, 113:307-315 (1993).

International Search Report dated Mar. 8, 2002 for International Application No. PCT/US00/41436.

Written Opinion dated Mar. 18, 2002 for International Application No. PCT/US00/41436.

Meda et al., "Activation of Microglial Cells by Beta-amyloid Protein and Interferon-gamma," *Nature 37*, 647-50 (1995).

Larner, "Neurite Growth-inhibitory Properties of Amyloid Beta-peptides in vitro: A beta 25-35, but not A Beta 1-40, is Inhibitory," *Neurosci Res. Commun.* 20(3): 147-155 (1997).

St. George-Hyslop et al, "Alzheimer's Disease. Antibody Clears Senile Plaques," *Nature 400*, 116-7 (1999).

\* cited by examiner (11)

(12)

(13)

(14)

(15)

(16)

PHARMACEUTICAL COMPOSITIONS USEFUL IN PREVENTION AND TREATMENT OF BETA-AMYLOID PROTEIN-INDUCED DISEASE

RELATED APPLICATIONS

This application is a Continuation of U.S. patent application Ser. No. 10/111,039 filed Apr. 19, 2002 now U.S. Pat. No. 6,887,898 which is the U.S. National Phase of International Patent Application Ser. No. PCT/US00/41436 filed Oct. 23, 2000 which claims priority from U.S. Provisional Patent Application Ser. No. 60/161,145 filed Oct. 22, 1999 the disclosure of which is hereby incorporated by reference.

BACKGROUND OF THE INVENTION

1. Field of the Invention

The invention relates to the use of natural product compounds isolated from plants, and synthetic chemical analogues thereof, for the prevention and treatment of beta-Amyloid protein-induced disease. More particularly, the invention relates to pharmaceutical compositions that protect neuronal cells from beta-Amyloid insult for use in preventing and treating beta-Amyloid protein-induced disease.

2. Description of Related Technology

Alzheimer's disease (AD) is the most common cause of progressive cognitive dysfunction. AD affects approximately four million Americans and causes more than 100,000 deaths each year, with a total annual cost approaching $70 billion. It is estimated that by the year 2020, 14 million Americans will be affected by the disease. Furthermore, AD has a profound effect on the millions of family members and other loved ones who provide most of the care for people having this disease. Unfortunately, the cure for AD has not been discovered.

The principal pathological characteristics of AD are senile plaques and neurofibrillary tangles (NFT's). Senile plaques are extracellular deposits, principally composed of insoluble aggregates of beta-Amyloid protein ($\beta$A protein), that are infiltrated by reactive microglia and astrocytes. Plaques are diffusely distributed throughout the cerebral cortex of AD patients, and are the neuropathologic hallmark of the disease. These plaques or fibril deposits are believed to be responsible for the pathology of a number of neurodegenerative diseases including, but not limited to, Alzheimer's disease. NFT's are intraneuronal accumulations of paired helical filaments, composed mainly of an abnormal form of tau protein, a microtubule associated phosphoprotein which can promote microtubule formation. In the AD brain, the tau protein in NFT is hyperphosphorylated, a condition which has been suggested to contribute to the destabilization of the microtubule network, thereby impairing the axonal network, and eventually causing neuronal death. NFT's occur primarily in medial temporal lobe structures (hippocampus, eniorhinal cortex, and amygdala), and NFT density appears to correlate with dementia severity.

Senile plaques and NFT's appear to be involved in cerebral amyloid angiopathy, consequent neuronal loss, and cerebral atrophy leading to dementia. Although research findings suggest that both plaques and NFT's are involved in disrupting nerve cell functions, the mechanisms that lead to the pathology are not clearly understood.

$\beta$-Amyloid peptide has been suggested as one of the major causes of AD. $\beta$A peptide (25-35) was shown to exert direct toxic effects on neurons and to inhibit neurite growth in vitro in a dose dependent manner. See Meda et al., Nature 374, 647 (1995) and Lamer, Neurosci. Res. Commun. 20, 147 (1997). Thus, therapeutic approaches that can modulate $\beta$A peptide toxicity have been hypothesized to represent important methods for controlling the onset of AD. It is envisioned that if neuronal cells can be protected from $\beta$A peptide/senile plaque-induced toxicity, the onset of AD may be delayed or prevented. Current pharmacological approaches related to AD preventive and neuroprotective interventions include nicotinic and muscarinic agonists, estrogen, calcium channel blockers, Zinc, sulfonated compounds, triaminopyridine nonopiate analgesic drugs, and non-steroidal anti-inflammatory drugs such as ibuprofen and aspirin. Of particular interest to the present invention is the observation that an anti-$\beta$A protein antibody was shown to clear senile plaques and protect mutant PDAPP mice from the onset of AD. See St. George-Hyslop et al., Nature 400, 116 (1999).

The generation of reactive oxygen intermediates through oxidative stress caused by $\beta$A peptide has been suggested to be the major pathway of $\beta$A peptide-induced cytotoxicity. Senile plaques have been shown to exert a cytotoxic effect on neurons by stimulating microglia to produce reactive oxygen species (ROS). The damaging effect of ROS can be prevented by the free radical scavenging enzyme superoxide dismutase.

Aging of synthetic $\beta$A peptide (1-42) for 7 to 14 days at 37° C. in modified Eagle's media was also demonstrated to cause neurotoxic free radical formation. However, aging $\beta$A peptide (1-42) in the presence of the media supplement B27, which contains antioxidants as well as other agents that provide protection against oxidative damage, has been shown to inhibit $\beta$A peptide-induced neuroloxicity. Nonetheless, while antioxidants such as propyl gallate, Trolox, Probucol, and Promethazine provide significant protection against oxidative insults, they do not protect against $\beta$A peptide insults. Furthermnore, it has been shown that $\beta$A peptide-induced lipid peroxidation does not contribute directly to cell death.

When the neuroprotective effect of lazaroids (U74389G and U83836E), 21-aminosteroids with antioxidant activity, were tested on cortical cells grown with or without fetal calf serum, U74389G did not protect the cells from $\beta$A peptide (25-35) insult in either condition, while low concentrations (15 nM) of U83836E protected the cells exposed to $\beta$A peptide in the presence of fetal calf serum. See Lucca et al., Brain Res., 764, 293 (1997). These data suggest that the primary mechanism by which these compounds protect cells from $\beta$A peptide-induced toxicity may not involve antioxidative pathways.

In addition to $\beta$A peptide-induced ROS mediated neurotoxicity, $\beta$A peptide has been shown to cause neuronal cell death by stimulating microglial expression of tumor necrosis factor a (TNF$\alpha$). The accumulation of $\beta$A peptide as neuritic plaques is known to be both trophic and toxic to hippocampal neurons, causing apoptosis or necrosis of the neurons in a dose dependent manner. $\beta$A peptide was demonstrated to induce these cellular effects by binding with a receptor for advanced glycation end products (RAGE) that was previously known as a central cellular receptor for advanced glycation endproducts. RAGE was suggested to mediate the interaction of $\beta$A peptide with neurons and with microglia, resulting in oxidative stress mediated cytotoxicity. Blocking RAGE with anti-RAGE F($\alpha\beta'$)$_2$ prevented the appearance of TNF$\alpha$ messenger RNA and diminished TNF$\alpha$ antigen to levels seen in untreated cells. Thus, it is postulated that RAGE mediates microglial activation by $\beta$A peptide by producing cytotoxic cytokines that cause neuronal damage in AD patients. In addition, RAGE was also demonstrated to specifically bind with βA peptide and mediate βA peptide-induced oxidative stress.

Cell receptors that bind to βA peptide have been identified. The low-affinity neurbtrophin receptor p75 (p75NTR) which belongs to the family of apoptotic receptors that generate cell-death signals on activation was found throughout the brains of AD patients. βA peptide was found to be a ligand for p75NTR, and to cause preferential apoplosis of neurons and normal neural crest-derived melanocytes that express p75NTR upon specifically binding to p75NTR.

Basal forebrain cholinergic neurons express the highest levels of p75NTR in the adult human brain and have been shown to be involved in AD. The expression of p75NTR by wild-type and mutant PC12 cells was shown to potentiate βA peptide-induced cell death. This interaction of βA peptide with p75NTR to mediate neuronal death in AD suggested a new target for therapeutic intervention.

Recently, ERAB which is overexpressed in neurons of the AD brain, was shown to bind with βA peptide to induce neuronal death in AD. Blocking ERAB with an antibody, anti-ERAB F(ab')$_2$, was found to reduce the βA peptide-induced cell death while ERAB overexpression increases βA peptide-induced cell death.

Nerve growth factor (NGF) is important for the survival and maintenance of central cholinergic neurons. Considerable evidence from animal studies suggests that NGF may be useful in reversing, halting, or at least slowing the progression of AD-related cholinergic basal forebrain atrophy. Administration of NGF was reported to attenuate degeneration of neurons and improve cognitive behavior in animals by stimulating central cholinergic neurons that are known to die during the development of AD. A clinical trial using intracranial infusion of NGF was reported to improve the patient's verbal episodic memory. Thus, attempting to counteract the degeneration of cholinergic neurons by NGF or compounds having neurotrophic properties may be a reasonable approach to treat AD. There are several different possible methods for stimulating NGF receptors, such as, NGF infusion, implantation of slow-release biodegradable pellets, using carrier-mediated transport across the blood-brain barrier, grafting NGF-producing cells, transferring genes directly to the brain, developing NGF receptor agonists, or controlling the endogenous NGF production.

In designing inhibitors of βA peptide toxicity, it was found that neither the alteration of the apparent secondary structure of βA peptide nor the prevention of βA peptide aggregation is required to abrogate the cytotoxicity of βA peptide. Nonetheless, inducing changes in aggregation kinetics and in higher order structural characteristics of βA peptide aggregates also proved to be effective in reducing βA peptide toxicity. See Sotoet al., *Neuroreport* 7, 721 (1996). Synthetic inhibitors that interact with βA peptide were shown to completely block βA peptide toxicity against PC12 cells, demonstrating that complete disruption of amyloid fibril formation is not necessary for abrogation of toxicity. It was also demonstrated that dipolar compounds such as phloretin and exifone that decrease the effective negative charge of membranes can prevent the association of βA peptide with negatively charged lipid vesicles and thereby prevent βA peptide-induced cytotoxicity. See Hertel et al., *Proc. Nail. Acad. Sci. USA* 94, 9412 (1997). These results suggest that βA peptide toxicity can be mediated through a physicochemical interaction with cell membranes.

There is strong interest in discovering potentially valuable natural products from natural sources for drug development. One reasonable source of such natural products involves medicinal plants that have been used throughout history for treating illness. Thus, the isolation of potentially valuable natural products from plants that can protect neurons from βA peptide insult is of interest. Although there are extensive reports that describe the extraction, fractionation, and chemical elucidation of natural products, plants have attracted relatively little attention as potentially valuable resources for drug discovery in the area of AD research. In order to achieve this goal, it is important to isolate and identify the chemical constituents in plants responsible for the biological activity.

Turmeric has been used as a curry spice and is used in traditional Indonesian medicine. Curcumin, a chemical constituent of turmeric, is an inhibitor of arachidonic acid metabolism and is a good anti-inflammatory agent. Curcumin is known to have antioxidative properties and has been shown to exhibit antitumor activity. Currently, curcumin is being evaluated as a chemopreventive agent by the National Cancer Institute.

*G. biloba* is a living fossil tree having undergone little evolutionary change over almost 200 million years. Extracts of the leaves have been used for 5,000 years in traditional Chinese medicine for various purposes. In 1994, a standardized dry extract of *Ginkgo biloba* leaves was approved by German health authorities for the treatment of primary degenerative dementia and vascular dementia. Currently, more than twenty four different brands of *G. biloba* extract are sold in the United States.

The use of complementary medications such as plant extracts in dementia therapy, varies according to different cultural traditions. In orthodox Western medicine, the pharmacological properties of traditional cognitive or memory enhancing plants have not been widely investigated in the context of current models of Alzheimer's disease. An exception is *Ginkgo biloba* L. in which the ginkgolides have been proposed to possess antioxidant, neuroprolective, and cholinergic activities relevant to Alzheimer's disease mechanisms. The leaves of *G. biloba* have been used as medicine for the treatment of peripheral or cerebral circulatory disorders, as well as for vascular and Alzheimer-type dementia. The therapeutic efficacy of *G. biloba* extracts in the treatment of Alzheimer's disease is reportedly similar to currently prescribed drugs such as tacrine or donepezil. See Maurer et al., *J. Psychiatr. Res.* 31, 645 (1997). In addition, the undesirable side effects of *G. biloba* are minimal. However, while there are more than two hundred articles published on the potential anti-AD effects of ginkgo products, the active constituents of the plant have not been isolated and identified.

Ginger is one of the world's favorite spices, and was probably discovered in the tropics of Southeast Asia. Ginger has benefitted humankind as a wonder drug since the beginning of recorded history.

It has been hypothesized that natural products capable of protecting neuronal cells from βA peptide insult can be discovered from plants, and specifically from turmeric, *ginkgo biloba*, and ginger. Although no anti-AD natural product derived drug that modulates βA peptide effect has been identified, historically, plants have been used for medicinal purposes that include alleviating the symptoms of AD. Among the medicinal plants suggested for the treatment of AD, *ginkgo biloba* and *Huperzia serrata* have been most extensively investigated. Huperzine A., a naturally occurring cholinesterase inhibitor from a moss *Huperzia serrata* is one natural product under development as a therapeutic agent to treat AD patients. See Skolnick, *JAMA* 277, 776 (1997). Further, a number of synthetic acetylcholinesterase inhibitors are under development as therapeutic agents against AD. However, while the published data indicate that the acetylcholinesterase inhibitor approach may be good for alleviating some of the symptoms of AD, such as improving memory, this approach does not cure or prevent the onset of the disease. Consequently, there remains a need to identify, isolate, and synthetically prepare new and improved anti-AD drugs which can provide chemotherapeutic and chemopreventive methods for the treatment of AD.

SUMMARY OF THE INVENTION

The present invention relates to the identification and isolation of natural compounds present in turmeric, ginger, and *gingko biloba* that exhibit potent anti-βA peptide activity. The invention further provides novel synthetic compounds exhibiting potent anti-βA peptide activity. Specifically, the invention provides compounds and pharmaceutical compositions capable of protecting neurons from βA peptide insult, and methods for treating βA protein-induced disease with the same.

In one aspect, the invention relates to a method for the treatment of a beta-Amyloid protein-induced disease comprising administering to a subject suffering from the beta-Amyloid protein-induced disease a therapeutically effective amount of a compound having the formula (I):

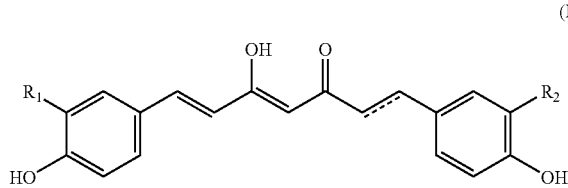

(I)

or a compound having the formula (II):

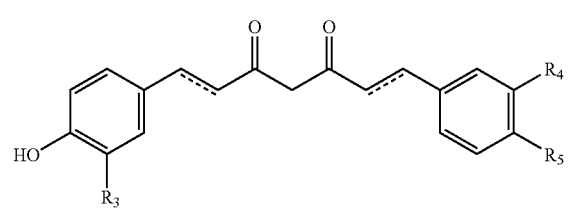

(II)

or a compound having the formula (III):

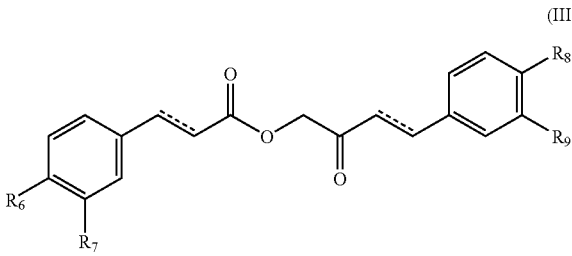

(III)

or pharmaceutically acceptable salts or esters thereof, wherein the dotted configuration

----- is optionally a single bond or a double bond, $R_1$ is selected from the group consisting of H, OH, OMe, and $OR_{50}$ wherein $R_{50}$ is alkyl, alkenyl, or alkynyl, $R_2$ is selected from the group consisting of H, OMe, and $OR_{50}$ wherein $R_{50}$ is alkyl, alkenyl, or alkynyl, $R_3$ is selected from the group consisting of H, OMe, and $OR_{50}$ wherein $R_{50}$ is alkyl, alkenyl, or alkynyl, $R_4$ is selected from the group consisting of H, OH, OMe, and $OR_{50}$ wherein $R_{50}$ is alkyl, alkenyl, or alkynyl, $R_5$ is selected from the group consisting of H, OH, OMe, $OR_{50}$, and X wherein $R_{50}$ is alkyl, alkenyl, or alkynyl, and X is F, Cl, Br, or I, $R_6$ is selected from the group consisting of OH, OMe, $OR_{50}$, and X wherein $R_{50}$ is alkyl, alkenyl, or alkynyl, and X is F, Cl, Br, or I, $R_7$ is selected from the group consisting of H, OMe, and $OR_{50}$ wherein $R_{50}$ is alkyl, alkenyl, or alkynyl, $R_8$ is selected from the group consisting of OH, OMe, $OR_{50}$ and X wherein $R_{50}$ is alkyl, alkenyl, or alkynyl, and X is F, Cl, Br, or I, and $R_9$ is selected from the group consisting of H, OMe, and $OR_{50}$ wherein $R_{50}$ is alkyl, alkenyl, or alkynyl.

In another aspect, the invention relates to a pharmaceutical composition comprising a purified and isolated compound having the formula (I), or a compound having the formula (II), or a compound having the formula (III) and a pharmaceutically acceptable diluent, adjuvant, or carrier wherein the dotted configuration

----- is optionally a single bond or a double bond, $R_1$ is selected from the group consisting of H, OH, OMe, and $OR_{50}$ wherein $R_{50}$ is alkyl, alkenyl, or alkynyl, $R_2$ is selected from the group consisting of H, OMe, and $OR_{50}$ wherein $R_{50}$ is alkyl, alkenyl, or alkynyl, $R_3$ is selected from the group consisting of H, OMe, and $OR_{50}$ wherein $R_{50}$ is alkyl, alkenyl, or alkynyl, $R_4$ is selected from the group consisting of H, OH, OMe, and $OR_{50}$ wherein $R_{50}$ is alkyl, alkenyl, or alkynyl, $R_5$ is selected from the group consisting of H, OH, OMe, $OR_{50}$, and X wherein $R_{50}$ is alkyl, alkenyl, or alkynyl, and X is F, Cl, Br, or I, $R_6$ is selected from the group consisting of OH, OMe, $OR_{50}$, and X wherein $R_{50}$ is alkyl, alkenyl, or alkynyl, and X is F, Cl, Br, or I, $R_7$ is selected from the group consisting of H, OMe, and $OR_{50}$ wherein $R_{50}$ is alkyl, alkenyl, or alkynyl, $R_8$ is selected from the group consisting of OH, OMe, $OR_{50}$ and X wherein $R_{50}$ is alkyl, alkenyl, or alkynyl, and X is F, Cl, Br, or I, and $R_9$ is selected from the group consisting of H, OMe, and OR, wherein $R_{50}$ is alkyl, alkenyl, or alkynyl.

In another aspect, the invention relates to a compound of formula (II) wherein the dotted configuration

----- is optionally a single bond or a double bond, $R_3$ is selected from the group consisting of H, OMe, and $OR_{50}$ wherein $R_{50}$ is alkyl, alkenyl, or alkynyl, $R_4$ is selected from the group consisting of H, OH, OMe, and $OR_{50}$ wherein $R_{50}$ is alkyl, alkenyl, or alkynyl, $R_5$ is selected from the group consisting of H, OH, OMe, $OR_{50}$, and X wherein $R_{50}$ is alkyl, alkenyl, or alkynyl, and X is F, Cl, Br, or I, wherein when both dotted configurations are double bonds and $R_5$ is OH, $R_3$ is selected from the group consisting of OMe and $OR_{50}$ wherein $R_{50}$ is alkyl, alkenyl, or alkynyl or $R_4$ is selected from the group consisting of OH and $OR_{50}$ wherein $R_{50}$ is alkyl, alkenyl, or alkynyl, and wherein when only one of the dotted configurations is a double bond and $R_5$ is OH, $R_3$ is selected from the group consisting of OMe and $OR_{50}$ wherein $R_{50}$ is alkyl, alkenyl, or alkynyl or $R_4$ is selected from the group consisting of OH and $OR_{50}$ wherein $R_{50}$ is alkyl, alkenyl, or alkynyl.

In another aspect, the invention relates to a compound of formula (III) wherein the dotted configuration

----- is optionally a single bond or a double bond, $R_6$ is selected from the group consisting of OH, OMe, $OR_{50}$, and X wherein $R_{50}$ is alkyl, alkenyl, or alkynyl, and X is F, Cl, Br, or I, $R_7$ is selected from the group consisting of H, OMe, and $OR_{50}$ wherein $R_{50}$ is alkyl, alkenyl, or alkynyl, $R_8$ is selected from the group consisting of OH, OMe, $OR_{50}$ and X wherein $R_{50}$ is alkyl, alkenyl, or alkynyl, and X is F, Cl, Br, or I, $R_9$ is selected from the group consisting of H, OMe, and $OR_{50}$ wherein $R_{50}$ is alkyl, alkenyl, or alkynyl and wherein when both dotted configurations are double bonds and $R_6$ is OH, $R_7$ is OMe, and $R_8$ is OH, $R_9$ is H.

In another aspect, the invention relates to the use of a compound having the formula (I), or a compound having the formula (II), or a compound having the formula (III) for the manufacture of a medicament for treatment of beta-Amyloid protein-induced disease wherein the dotted configuration

----- is optionally a single bond or a double bond, $R_1$ is selected from the group consisting of H, OH, OMe, and $OR_{50}$ wherein $R_{50}$ is alkyl, alkenyl, or alkynyl, $R_2$ is selected from the group consisting of H, OMe, and $OR_{50}$ wherein $R_{50}$ is alkyl, alkenyl, or alkynyl, $R_3$ is selected from the group consisting of H, OMe, and $OR_{50}$ wherein $R_{50}$ is alkyl, alkenyl, or alkynyl, $R_4$ is selected from the group consisting of H, OH, OMe, and $OR_{50}$ wherein $R_{50}$ is alkyl, alkenyl, or alkynyl, $R_5$ is selected from the group consisting of H, OH, OMe, $OR_{50}$, and X wherein $R_{50}$ is alkyl, alkenyl, or alkynyl, and X is F, Cl, Br, or I, $R_6$ is selected from the group consisting of OH, OMe, $OR_{50}$, and X wherein $R_{50}$ is alkyl, alkenyl, or alkynyl, and X is F, Cl, Br, or I, $R_7$ is selected from the group consisting of H, OMe, and $OR_{50}$ wherein $R_{50}$ is alkyl, alkenyl, or alkynyl, $R_8$ is selected from the group consisting of OH, OMe, $OR_{50}$ and X wherein $R_{50}$ is alkyl, alkenyl, or alkynyl, and X is F, Cl, Br, or I, and $R_9$ is selected from the group consisting of H, OMe, and $OR_{50}$ wherein $R_{50}$ is alkyl, alkenyl, or alkynyl.

Yet another aspect of the invention relates to a method for the treatment of a beta-Amyloid protein-induced disease comprising administering to a subject suffering from the beta-Amyloid protein-induced disease a therapeutically effective amount of a compound having the formula (IV):

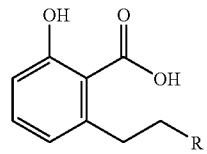

(IV)

or a pharmaceutically acceptable salt or ester thereof, wherein R is selected from the group consisting of higher alkyl, higher alkenyl, and higher alkynyl.

In addition, the invention can relate to a pharmaceutical composition comprising a purified and isolated compound having the formula (IV) and a pharmaceutically acceptable diluent, adjuvant, or carrier, wherein R is selected from the group consisting of higher alkyl, higher alkenyl, and higher alkynyl.

In yet another aspect, the invention relates to the use of a compound having the formula (IV) for the manufacture of a medicament for treatment of a beta-Amyloid protein-induced disease wherein R is selected from the group consisting of higher alkyl, higher alkenyl, and higher alkynyl.

The invention also relates to a method for the treatment of a beta-Amyloid protein-induced disease comprising administering to a subject suffering from the beta-Amyloid protein-induced disease a therapeutically effective amount of a compound having the formula (V):

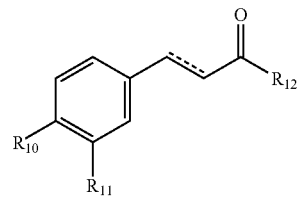

(V)

or a pharmaceutically acceptable salt or ester thereof, wherein the dotted configuration

----- is optionally a single bond or a double bond, $R_{10}$ is selected from the group consisting of OH, OMe, OR', and X wherein R' is alkyl, alkenyl, or alkynyl, and X is F, Cl, Br, or I, $R_{11}$ is selected from the group consisting of H, OH, OMe, and OR' wherein R' is alkyl, alkenyl, or alkynyl, and $R_{12}$ is selected from the group consisting of alkyl, alkenyl, and alkynyl.

In another aspect, the invention relates to a pharmaceutical composition comprising a purified and isolated compound having the formula (V) and a pharmaceutically acceptable diluent, adjuvant, or carrier, wherein the dotted configuration

----- is optionally a single bond or a double bond, $R_{10}$ is selected from the group consisting of OH, OMe, OR', and X wherein R' is alkyl, alkenyl, or alkynyl, and X is F, Cl, Br, or I, $R_{11}$ is selected from the group consisting of H, OH, OMe, and OR' wherein R' is alkyl, alkenyl, or alkynyl, and $R_{12}$ is selected from the group consisting of alkyl, alkenyl, and alkynyl.

In another aspect, the invention relates to a compound of formula (V) wherein the dotted configuration

----- is optionally a single bond or a double bond, $R_{10}$ is selected from the group consisting of OH, OMe, OR', and X wherein R' is alkyl, alkenyl, or alkynyl and X is F, Cl, Br, or I, $R_{11}$ is selected from the group consisting of H, OH, OMe, and OR' wherein R' is alkyl, alkenyl, or alkynyl, and $R_{12}$ is selected from the group consisting of alkyl, alkenyl, and alkynyl, and wherein when $R_{12}$ is

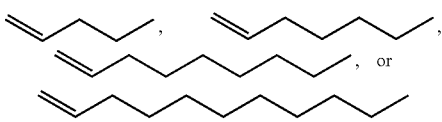

$R_{10}$ is selected from the group consisting of OMe, OR', and X wherein R' is alkyl, alkenyl, or alkynyl, and X is F, Cl, Br, or I, or $R_{11}$ is selected from the group consisting of H, OH, and OR' wherein R' is alkyl, alkenyl, or alkynyl.

In yet another aspect, the invention relates to the use of a compound having the formula (V) for the manufacture of a medicament for treatment of a beta-Amyloid protein-induced disease wherein the dotted configuration

----- is optionally a single bond or a double bond, $R_{10}$ is selected from the group consisting of OH, OMe, OR', and X wherein R' is alkyl, alkenyl, or alkynyl, and X is F, Cl, Br, or I, $R_{11}$ is selected from the group consisting of H, OH, OMe, and OR' wherein R' is alkyl, alkenyl, or alkynyl, and $R_{12}$ is selected from the group consisting of alkyl, alkenyl, and alkynyl.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
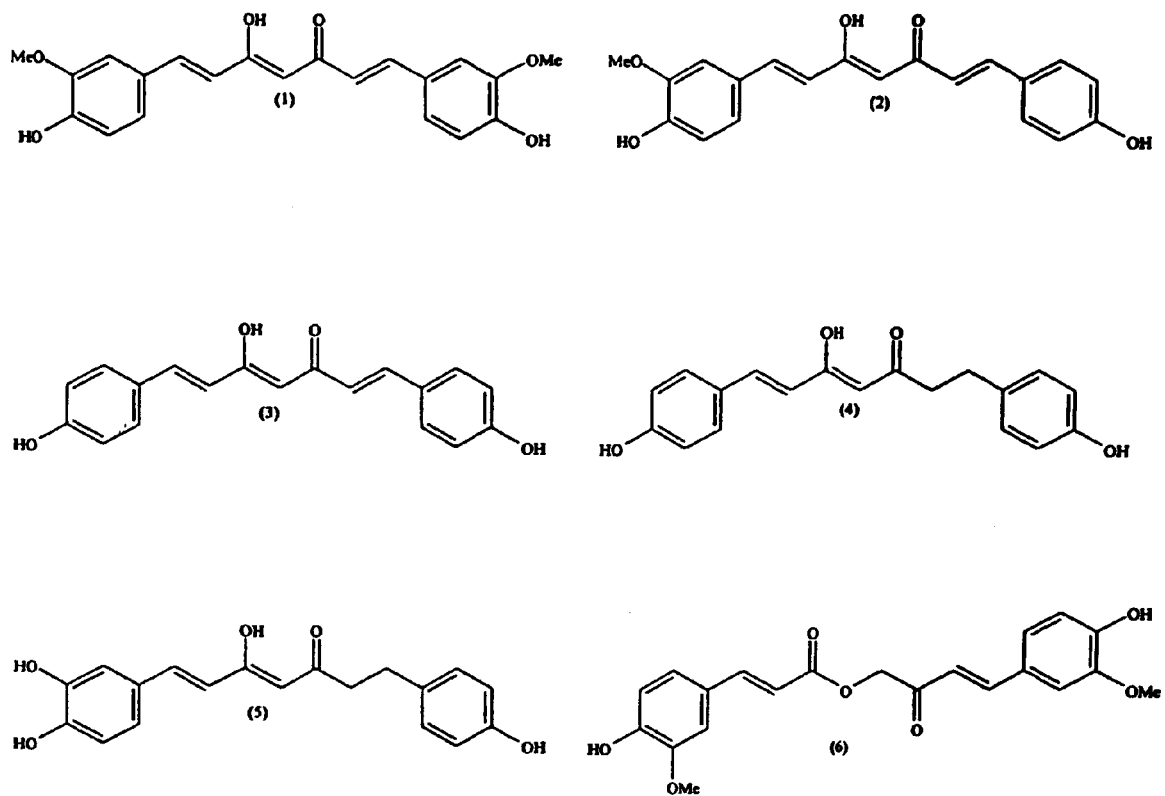
FIG. 1 shows the structures of turmeric-derived natural product compounds that protected PC12, IMR32, and HUVEC cells from βA peptide-induced toxicity.

One aspect of the present invention is directed to the use of methanol and other extracts of turmeric, ginger, and *ginkgo biloba* characterized by their ability to effectively protect cells from βA peptide insult. Via bio-assay guided fractionation, twelve natural product compounds (eleven known and one novel) exhibiting potent anti-βA peptide activity were isolated and identified. These natural product compounds were found to protect PC12, IMR32, HUVEC, and primary cortical rat neuronal cells from βA peptide (both 25-35 and 1-42) insult.

In some cases, the natural product compounds were synthetically prepared. It is necessary and cost efficient to chemically synthesize the compounds in order to perform a thorough bioassay because only a small amount of these compounds are available from the natural sources. The biological activities of the synthesized natural product compounds were identical to those of the natural product compounds isolated from the plants. A series of natural product analogues that protect cells from βA peptide insult as effectively as the isolated natural product compounds were also synthesized.

Methods of treating a beta-Amyloid protein-induced disease with the compounds of the invention are described herein. Further, pharmaceutical compositions comprising one or more compounds of the invention and a pharmaceutically acceptable diluent, adjuvant, or carrier are provided. The use of the compounds of the invention for the manufacture of a medicament for treatment of a beta-Amyloid protein-induced disease is also disclosed herein.

Natural product compounds having the following general formula were isolated from turmeric and were found to protect cells from βA peptide insult. In addition, several of the natural product compounds described by this general formula were synthetically prepared.

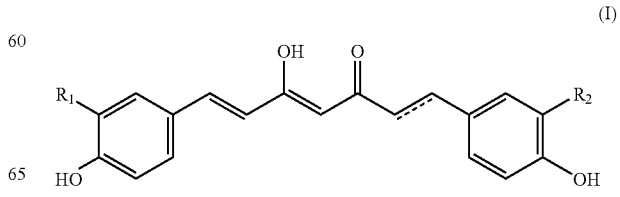

In this formula, the dotted configuration is optionally a single bond or a double bond. Generally, $R_1$ is selected from the group consisting of H, OH, OMe, and $OR_{50}$ wherein $R_{50}$ is alkyl, alkenyl, or alkynyl. Preferably, $R_1$ is selected from the group consisting of H, OH, OMe, and $OR_{60}$ wherein $R_{60}$ is $(CH_2)_nCH_3$ and n is 1-7. More preferably, $R_1$ is selected from the group consisting of H, OH, and OMe. Even more preferably, $R_1$ is selected from the group consisting of H and OMe when the dotted configuration of compound (I) is a double bond, and $R_1$ is selected from the group consisting of H and OH when the dotted configuration is a single bond. Generally, $R_2$ is selected from the group consisting of H, OMe, and $OR_{50}$ wherein $R_{50}$ is alkyl, alkenyl, or alkynyl. Preferably, $R_2$ is selected from the group consisting of H, OMe, and $OR_{60}$ wherein $R_{60}$ is $(CH_2)_nCH_3$ and n is 1-7. More preferably, $R_2$ is selected from the group consisting of H and OMe. Even more preferably, $R_2$ is selected from the group consisting of H and OMe when the dotted configuration of compound (I) is a double bond, and $R_2$ is H when the dotted configuration is a single bond.

Compounds having the following general formula were successfully synthesized and were found to protect cells from βA peptide-induced todxicity.

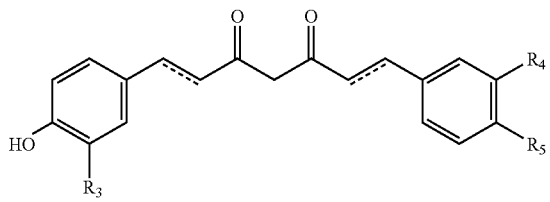

(II)

In this formula, the dotted configuration is optionally a single bond or a double bond. Generally, $R_3$ is selected from the group consisting of H, OMe, and $OR_{50}$ wherein $R_{50}$ is alkyl, alkenyl, or alkynyl. Preferably, $R_3$ is selected from the group consisting of H, OMe, and $OR_{60}$ wherein $R_{60}$ is $(CH_2)_nCH_3$ and n is 1-7. More preferably, $R_3$ is selected from the group consisting of H and OMe. Even more preferably, $R_3$ is H. Generally, $R_4$ is selected from the group consisting of H, OH, OMe, and $OR_{50}$ wherein $R_{50}$ is alkyl, alkenyl, or alkynyl. Preferably, $R_4$ is selected from the group consisting of H, OH, OMe, and $OR_{60}$ wherein $R_{60}$ is $(CH_2)_nCH_3$ and n is 1-7. More preferably, $R_4$ is selected from the group consisting of H, OH, and OMe. Even more preferably, $R_4$ is H when the first dotted, configuration of compound. (II) is a double bond and the second dotted configuration of compound (II) is a single bond, $R_4$ is H when both dotted configurations are single bonds, and $R_4$ is selected from the group consisting of H and OMe when both dotted configurations are double bonds. Generally, $R_5$ is selected from the group consisting of H, OH, OMe, $OR_{50}$, and X wherein $R_{50}$ is alkyl, alkenyl, or alkynyl, and X is F, Cl, Br, or I. Preferably, $R_5$ is selected from the group consisting of H, OH, OMe, $OR_{60}$, and X wherein $R_{60}$ is $(CH_2)_nCH_3$ and n is 1-7, and X is F, Cl, Br, or I. More preferably, $R_5$ is selected from the group consisting of H, OH, and OMe. Even more preferably, $R_5$ is OH.

While compounds of formula (II) have been presented herein as diketones, and compounds of formula (I) have been presented as enols, those of skill in the art recognize that diketones and enols can coexist in solution as tautomers as shown below.

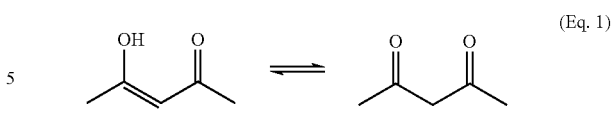

(Eq. 1)

Accordingly, the invention contemplates the use and production of compounds in either tautomeric form, and as a mixture of the two forms.

A natural product compound having the following general formula was isolated from turmeric, and was found to protect cells from βA peptide-induced toxicity. In addition, one of the compounds described by this formula was synthetically prepared.

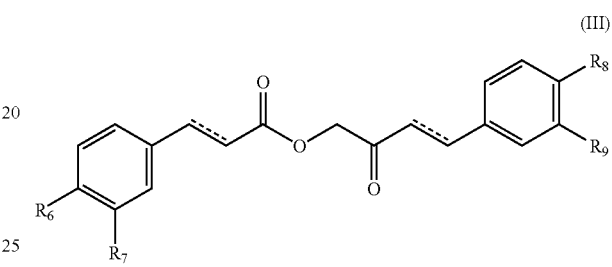

(III)

In this formula, the dotted configuration is optionally a single bond or a double bond. Generally, $R_6$ is selected from the group consisting of OH, OMe, $OR_{50}$, and X wherein $R_{50}$ is alkyl, alkenyl, or alkynyl, and X is F, Cl, Br, or I. Preferably, $R_6$ is selected from the group consisting of OH, OMe, $OR_{60}$ and X wherein $R_{60}$ is $(CH_2)_nCH_3$ and n is 1-7 and X is F, Cl, Br, or I. More preferably, $R_6$ is selected from the group consisting of OH and OMe. Even more preferably, $R_6$ is OH. Generally, $R_7$ is selected from the group consisting of H, OMe, and $OR_{50}$ wherein $R_{50}$ is alkyl, alkenyl, or alkynyl. Preferably, $R_7$ is selected from the group consisting of H, OMe and $OR_{60}$ wherein $R_{60}$ is $(CH_2)_nCH_3$ and n is 1-7. More preferably, $R_7$ is selected from the group consisting of H and OMe. Even more preferably, $R_7$ is OMe. Generally, $R_8$ is selected from the group consisting of OH, OMe, $OR_{50}$ and X wherein $R_{50}$ is alkyl, alkenyl, or alkynyl, and X is F, Cl, Br, or I. Preferably, $R_8$ is selected from the group consisting of OH, OMe, $OR_{60}$ and X wherein $R_{60}$ is $(CH_2)_nCH_3$ and n is 1-7, and X is F, Cl, Br, or I. More preferably, $R_8$ is selected from the group consisting of OH and OMe. Even more preferably, $R_8$ is OH. Generally, $R_9$ is selected from the group consisting of H, OMe and $OR_{50}$ wherein $R_{50}$ is alkyl, alkenyl, or alkynyl. Preferably, $R_9$ is selected from the group consisting of H, OMe and $OR_{60}$ wherein $R_{60}$ is $(CH_2)_nCH_3$ and n is 1-7. More preferably, $R_9$ is selected from the group consisting of H and OMe. Even more preferably, $R_9$ is OMe.

Natural product compounds having the following general formula were isolated from *ginkgo biloba* and were found to protect cells from βA peptide-induced toxicity.

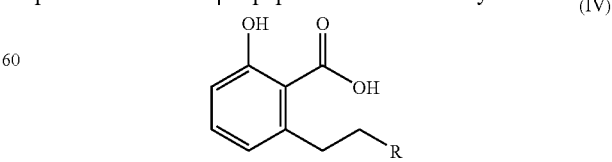

(IV)

In this formula, R is preferably selected from the group consisting of higher alkyl, higher alkenyl, and higher alkynyl. More preferably, R is

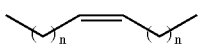

and n is 1-7. Even more preferably, R is selected from the group consisting of

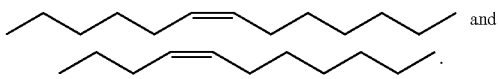

Natural product compounds having the following general formula were isolated from ginger and were found to protect cells from βA peptide-induced toxicity.

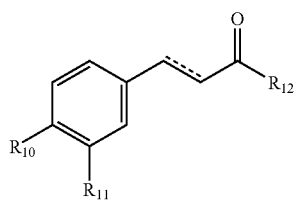

(V)

In this formula, the dotted configuration is optionally a single bond or a double bond. Preferably, $R_{10}$ is selected from the group consisting of OH, OMe, OR', and X wherein R' is alkyl, alkenyl, or alkynyl, and X is F, Cl, Br, or I. More preferably, $R_{10}$ is selected from the group consisting of OH, OMe, OR", and X wherein R" is $(CH_2)_n CH_3$ and n is 1-7, and X is F, Cl, Br, or I. Even more preferably, $R_{10}$ is OH. Preferably, $R_{11}$ is selected from the group consisting of H, OH, OMe, and OR' wherein R' is alkyl, alkenyl, or alkynyl. More preferably, $R_{11}$ is selected from the group consisting of H, OH, OMe, and OR" wherein R" is $(CH_2)_n CH_3$ and n is 1-7. Even more preferably, $R_{11}$ is selected from the group consisting of H and OMe. Preferably, $R_{12}$ is selected from the group consisting of alkyl, alkenyl, and alkynyl. More preferably, $R_{12}$ is selected from the group consisting of

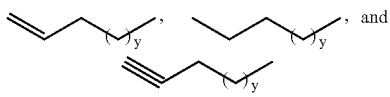

and y is 1-9. Even more preferably, $R_{12}$ is selected from the group consisting of

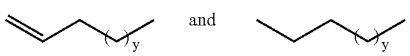

and y is 1-9.

It is apparent from the biological results for the ginger-derived natural product compounds that the length of the side chain is important for the expression of biological activity. For example, with respect to the ginger-derived natural product compounds, compounds (11), (12), (13), and (14), the biological activity appears to improve as the compounds' side chain length increases (Table 3). Thus, it is of interest to prepare analogues having different and lengthier side-chains. Preferably, shogaol compounds have side chains wherein $R_{12}$ has five or more carbons. More preferably, $R_{12}$ has nine or more carbons, and even more preferably, $R_{12}$ has eleven or more carbons. Furthermore, two of the synthesized shogaol analogue compounds, compounds (45) and (50), also effectively protected cells from βA peptide insult despite the fact that these compounds have different substituents than the ginger-derived natural product compounds. For example, compound (45) differs from the ginger-derived natural product compounds because it has a saturated hydrocarbon side chain, and compound (50) differs from the ginger-derived natural product compounds because it does not have a methoxy substituent. These data suggest that changing the nature of the substituents on the phenyl rings of the active compounds is of interest for the methods, pharmaceutical compositions, compounds and uses according to the invention.

As used herein, the term "alkyl" refers to a carbon chain having at least two carbons. Preferably, alkyl refers to a carbon chain having between two and twenty carbons. More preferably, alkyl refers to a carbon chain having between two and eight carbons. The term "alkenyl", as used herein, refers to a carbon chain having at least two carbons, and at least one carbon-carbon double bond. Preferably, alkenyl refers to a carbon chain having between two and twenty carbons, and at least one carbon-carbon double bond. More preferably, the term alkenyl refers to a carbon chain having between two and eight carbons, and at least one carbon-carbon double bond. The term "alkynyl", as used herein, refers to a carbon chain having at least two carbon atoms, and at least one carbon-carbon triple bond. Preferably, alkynyl refers to a carbon chain having between two and twenty carbon atoms, and at least one carbon-carbon triple bond. More preferably, alkynyl refers to a carbon chain having between two and eight carbon atoms, and at least one carbon-carbon triple bond.

As used herein, the term "higher alkyl" refers to a carbon chain having at least five carbon atoms. Preferably, higher alkyl refers to a carbon chain having between five and twenty carbons. More preferably, higher alkyl refers to a carbon chain having between five and twelve carbon atoms. As used herein, the term "higher alkenyl" refers to a carbon chain having at least five carbon atoms, and at least one carbon-carbon double bond. Preferably, higher alkenyl refers to a carbon chain having between five and twenty carbon atoms, and at least one carbon-carbon double bond. More preferably, higher alkenyl refers to a carbon chain having between five and twelve carbon atoms, and at least one carbon-carbon double bond. The term "higher alkynyl", as used herein, refers to a carbon chain having at least five carbons, and at least one carbon-carbon triple bond. Preferably, higher alkynyl refers to a carbon chain having between five and twenty carbon atoms, and at least one carbon-carbon triple bond. More preferably, the term higher alkynyl refers to a carbon chain having between five and twelve carbon atoms, and at least one carbon-carbon triple bond.

The administration of the natural product and natural product analogue compounds of the invention is preferably accomplished with a pharmaceutical composition comprising a therapeutically effective amount of an active compound of the present invention and a pharmaceutically acceptable diluent, adjuvant, or carrier. A compound according to the invention may be administered without or in conjunction with known antibiotics, surfactants, or other therapeutic agents. It is contemplated that the pharmaceutical compositions of this invention can be administered to humans and other animals orally, rectally, parentally, intracisternally, intraperitoneally, topically (as by powders, ointments, or drops), bucally, intranasally, or by any other effective route of administration.

According to the methods for treatment of the present invention, βA protein-induced disease is treated in a subject, such as a human or lower mammal, by administering to the subject a therapeutically effective amount of an active compound of the invention in such amounts and for such time as is necessary to achieve the desired results. The term "beta-Amyloid protein-induced disease", as used herein, refers to disease states that are characterized by the formation and aggregation of beta-Amyloid protein or beta-Amyloid peptide fibril deposits or plaques, such as, for example, Alzheimer's disease and Down's syndrome.

It is contemplated that the methods for treatment in accordance with the invention encompass the treatment of subjects wherein the βA protein-induced disease process is ongoing but wherein the subjects do not exhibit manifest outward symptoms, and/or wherein the pathology of the disease can not be detected using presently available technologies. Furthermore, the methods for treatment of the present invention contemplate not only treating the common symptoms associated with βA protein-induced diseases but also treating the pathology of the disease. Thus, the methods for treatment provided herein include treating symptoms associated with βA protein-induced diseases, such as, for example, the memory loss and dementia associated with Alzheimer's disease, but also include preventing senile plaque formations, and/or clearing such formations. It is hypothesized that the formation of senile plaques is a regularly occurring and ongoing process in humans and other mammals. However, it is further hypothesized that the equilibrium of this process is substantially disturbed in patients affected by βA protein-induced diseases, resulting in the accumulation and formation of senile plaques.

As used herein, the term "therapeutically effective amount" means that amounts of a compound of the present invention sufficient to alleviate, ameliorate, prevent, and/or clear the symptoms and/or the pathology of βA protein-induced disease are contemplated for administration. Accordingly, the methods for treatment of AD in accordance with the invention contemplate administration of an active compound of the invention whether βA protein-induced disease-like symptoms are manifest, or not.

The total daily dose of natural product compound (6) of this invention to be administered to a human or other mammal is preferably between 1 to 100 mg/kg body weight. More preferably, the total daily dosage is between 20 to 80 mg/kg body weight. Even more preferably, the total daily dosage is between 40 to 60 mg/kg body weight. One skilled in the art could obtain preferred dosage ranges for the other compounds of the invention by extrapolating from the compounds' $ED_{50}$ values, such as, for example the $ED_{50}$ values presented in Tables 1, 2, 3, and 4. It will be understood that the total daily usage of the compounds and compositions of the present invention will be decided by the attending physician within the scope of sound medical judgment. The specific therapeutically effective dose level for any particular patient will depend upon a variety of factors including the severity and progression of the disease, the time of administration, the route of administration, the size of the subject, the rate of excretion of the specific compound employed, the duration of the treatment, the additional therapeutic agents used in combination with the specific, compound of the invention, and like factors well known in the medical arts.

The mechanism of action of the natural product compounds and the natural product analogue compounds of the invention appears to involve both antioxidant and non-antioxidant pathways. Interestingly, two of the turmeric-derived natural product compounds, natural product compounds (4) and (6), induced neurite generation in PC12 cells (NGF-like neurotrophic effect), and this effect was more extensive than that of NGF in 24 hours. These two compounds constitute the first examples of plant-derived natural product compounds that possess neurotrophic properties. Without intending to be bound by a theory of the mechanism of the invention, it is believed that the compounds and compositions of the invention provide therapeutic and preventive agents that protect neurons from βA peptide insult by (1) an antioxidant pathway, (2) preventing the aggregation of βA peptide by directly binding to βA peptide, thereby altering its structural conformation and rendering it non-toxic, (3) binding to a receptor site on the cell, thereby altering the cell function in such a way that it is protected from βA peptide toxicity, or (4) a NGF-like neurotrophic effect.

The invention can be better understood in light of the following examples which are intended as an illustration of the practice of the invention and are not meant to limit the scope of the invention in any way.

EXAMPLE 1

Isolation and Identification of Natural Product Compounds Derived from Turmeric that Protect Cells from Beta Amyloid-induced Toxicity According to this example, potent anti-AD natural product compounds that protect cells from βA peptide-induced toxicity were isolated from turmeric by following bioassay-guided fractionation schemes. Briefly, ground turmeric was extracted with 90% methanol overnight (2×), and the solvent was removed under vacuum at 35° C. The residue was partitioned between petroleum ether/water, dichloromethane/water, and ethyl acetate/water, successively. After removing the solvents under vacuum at 35° C., the residues from each partition were screened for inhibitory activity against βA peptide-induced cytotoxicity using the MTT assay described in this example. The active principles were isolated from the residues of the active fractions by a series of column chromatography using various resins (Amberchrom non-ionic resin and silica gel) and semi-preparative HPLC reverse-phased separation (isopropyl alcohol/water or acetonitrile/water solvent system). Six curcuminoids, natural product compounds (1), (2), (3), (4), (5), and (6) were isolated from turmeric, and their structures were elucidated using NMR (1-D and 2-D $^1H$, $^{13}C$, APT, HMBC) and mass spectrum analysis. These compounds are shown in FIG. 1.

The inhibitory activity of the residues and of the identified compounds was determined by observing the differences in the cell viability of βA peptide (both 25-35 and 1-42) treated cells, βA peptide (both 25-35 and 1-42) treated cells further including a compound according to the invention, and a DMSO control.

The βA peptide-induced cytotoxic effect was measured by 3-[4, 5-dimethylthiazol-2-yl] 2, 5-diphenyltetrazoliun bromide (MTT) reduction assay. Mosmann described the general principle involved in the detection of cell growth or cell death by observing the conversion of MTT to the colored product, MTT formazan, the concentration of which can be measured colorimetrically at 550 nm. See Mosmann, T. *J. Immunol. Methods* 65,55-63 (1983) and Hansen et al. *J. Immunol. Methods* 119,203-210 (1989).

The βA peptide-induced toxicity inhibitory effects of the compounds were tested on PC12 cells. The cells were incubated with βA peptide (25-35) (1.0 μg/ml, made from 1.0 mg/ml stock solution in DMSO) or βA peptide (1-42) (2.0 μg/ml, made from 1.0 mg/ml stock solution in DMSO) and the test compounds at various concentrations (25, 5.0, 1.0, and 0.2 μg/ml) in collagen-coated 96-well tissue culture plates for 24 hours. The βA peptide-induced toxicity inhibitory effect of the compounds was determined by colorimetrically and microscopically evaluating the PC12 cells' potential to reduce MTT against a positive control (1% DMSO only) and a negative control (1.0 μg/ml βA peptide in 1% DMSO alone). Cells were incubated in MTT solution (5 mg/ml) at 37° C. for 2 hours. During this time, cells were observed under a microscope every 15 min. Cells were incubated in Lysing buffer (100 μl) overnight at 37° C. Colorimetric determination of MTT reduction was made at 550 nm. The βA peptide-induced cytotoxicity inhibitory activity of the compounds was also evaluated against IMR32, HUVEC, and primary cortical rat neuronal cells.

PC12 rat pheochromocytoma and IMR32 human neuroblastoma cells were obtained from the American Type Culture Collection (ATCC). HUVEC normal umbilical human vein endothelial cells were obtained from Clonetics (San Diego, Calif.). Cells were routinely cultured on a tissue culture plate (Corning, New York, N.Y.). PC12 cells were grown in high glucose Dulbecco's Modified Eagle Medium (DMEM), 10% horse serum, 5% fetal calf serum, and 1% penicillin/streptomycin. IMR32 cells were grown in 90% DMEM and 10% fetal calf serum with 1% penicillin/streptomycin. HUVEC cells were grown in EGM-2 Bullet Kit (Clonetics, San Diego, Calif.). For the bioassay using βA peptide(25-35) and βA peptide(1-42), 100 μl of exponentially growing PC12 cells (2,000 cells per ml) were plated in collagen-coated 96-well tissue culture plates.

PC12 cells were cultured routinely on polystyrene-coated Corning tissue culture plates. PC12 cells gave consistent results only when the collagen-coated 96-well plates were used. The 96-well plates were coated with rat tail collagen (Boehringer Mannheim) in order to promote uniform PC12 cell attachment and growth. Under the experimental conditions, βA peptide(25-35) and βA peptide(1-42) was toxic to PC12 cells at $ED_{50}$=1.0 and 5.0 μg/ml, respectively.

IMR32 and HUVEC cells were chosen to confirm and supplement the anti-βA peptide activity of the compounds identified by the assay using PC12 cells. βA peptide has been reported to be cytotoxic to IMR32 and endothelial cells. Experimental results demonstrated that IMR32 and HUVEC cells are sensitive to βA peptide (25-35) at $ED_{50}$=3.0 and 6.0 μg/ml, respectively, and βA peptide (1-42) at $ED_{50}$=6.0 and 10.0 μg/ml, respectively.

Dissociated primary neuronal cell cultures were established from 18-day-old Sprague-Dawley rat fetuses. The pups were delivered by caesarean section while the dam was anesthetized with ether. Hippocampal tissue from embryonic day 18 Sprague-Dawley rat pups was dissected and then rinsed in cold $Ca^{2+}/Mg^{2+}$-free Hank's balanced salt solution supplemented with 20 mM HEPES, 4.2 mM sodium bicarbonate, 1 mM pyruvate, and 3 mg/ml bovine serum albumin (BSA). Following gentle trituration of the tissue with a constricted pipette in cold buffer, two volumes of 10% fetal bovine serum (FBS) in DMEM were added to the suspension. After the suspension settled for 2 minutes, the supernatant was collected and centrifuged for 2 min. at 200×g. The cell pellets were resuspended in serum-free DMEM (pH 7.3), supplemented with 2.4 mg/ml BSA and a modification of Brewer's B16 defined components (with 250 nM vitamin B12 and without catalase, glutathione, and superoxide dismutase). Cells were plated at a density of 15,000 cells/cm² and grown at 37° C. After 24 hours of incubation to allow cell attachment, the serum-containing medium was replaced by defined medium with DMEM/F12 containing bovine transferrin (100 μg/ml), bovine insulin (5 μg/ml), putrescine (0.1 mM), progesterone (10 nM), sodium selenite (30 nM), sodium pyruvate (1 mM), and potassium bicarbonate (15 mM). Cells maintained for extended periods of time were fed twice a week by replacing ⅓ of the medium with fresh medium.

EXAMPLE 2

Inhibitory Activity and Antioxidant Potency of Turmeric-derived Natural Product Compounds Against Beta Amyloid Toxicity According to this example, the inhibitory activity of the turmeric-derived natural product compounds (1), (2), (3), (4), (5), and (6) (shown in FIG. 1) against βA peptide-induced toxicity was measured by the MTT reduction assay described in example 1. These six turmeric-derived curcuminoids protected PC12, IMR32, and HUVEC cells from βA peptide-induced toxicity (Table 1). These compounds also protected primary cortical neuronal cells at 5 μg/ml against βA peptide(1-42) insult (10 μg/ml).

$ED_{50}$ values reflect the results from the MTT assay, and represent the sample concentration that is required to achieve 50% cell viability, a mid-point between the positive control values and the negative control values. The samples that gave values as determined by the MTT assay less than or equal to that of βA peptide treated wells were considered cytotoxic or without desired activity, and are labeled "toxic".

The measurement of lactate dehydrogenase activity released to the extracellular bathing media was also used to assess cell viability in cell culture. LDH activity in the medium was measured by a method described by Koh and Choi. See Koh et al., *J. Neurosci. Methods* 20, 83 (1987). This assay was used to confirm the $ED_{50}$ results obtained in the MTT assay. Samples of media from 96-well cell culture plates were transferred to an empty well of a 96-well plate (100 μl) and 2.0 μmol of sodium pyruvate and 0.1 mg of the reduced form of nicotinamide adenine dinucleotide (NADH in 0.1 M $K_2PO_4$ buffer (pH 7.5 at 25° C.) were added (total volume of 400 μl). The absorbance of the reaction mixture at 340 nm provides an index of NADH concentration, and was recorded using a spectrophotometer 5 minutes after mixing the reagents. The experiment was performed in triplicate and the LDH concentration was calculated from the slope of the absorbance curve, fit by linear regression to the linear (initial) portion of the curve. The concentration of LDH was expressed in conventional units (u) per ml. Accuracy of the assay was verified by periodic checks of a standard LDH enzyme solution (Sigma).

$IC_{50}$ values reflect the results of the antioxidant assay described in this example, and represent the sample concentration which is required to scavenge 50% of the DPPH free radicals.

Using an antioxidant assay, the antioxidant potency of the compounds of the invention was evaluated. 1,1-Diphenyl-2-picrylhydrazyl (DPPH) is known to generate stable free radicals in aqueous and ethanolic solutions. The ability of the compounds of the invention to scavenge these free radicals was measured by observing the optical density change of DPPH radicals at 515 nm. See Smith et al., *Biochem. Pharmacol.* 36, 1457 (1987).

The samples were prepared in various concentrations (200, 20, 2.0, and 0.2 μg/ml) by serial dilution of a stock solution (5 mg/ml) and were tested by the following procedure. Reaction mixtures containing test compounds (dissolved in DMSO) and 300 μM DPPH ethanolic solution in 96-well microtiter plates were incubated at 37° C. for 30 min. and absorbance was measured at 515 nm. Percent inhibition by sample treatment was determined by comparison with a DMSO-treated positive control group. $IC_{50}$ values were determined from percent inhibition by sample. $IC_{50}$ values denote the concentration of the tested compound that was required to scavenge 50% of the DPPH free radicals.

The antioxidant potency of the natural product compounds was evaluated by measuring the compounds' ability to scavenge free radicals in order to elucidate the possible involvement of antioxidant pathways in the compounds ability to protect the cells (Tables 1 and 2). The results showed that only compounds (1) and (2) have strong antioxidant activity, suggesting that the compounds of the invention, may be protecting cells from βA peptide insults through a mechanism that does not involve an antioxidant pathway.

TABLE 1

Inhibitory Activity of Turmeric-Derived Natural Product Compounds against βA Peptide-Induced Toxicity against PC12, IMR32, and HUVEC cells and Antioxidant Activity of the Compounds.

| Compound | Anti-βA peptide (25-35) $ED_{50}$ (μg/ml) PC12 | Anti-βA peptide (1-42) $ED_{50}$ (μg/ml) PC12 | Anti-βA peptide (25-35) $ED_{50}$ (μg/ml) IMR32 | Anti-βA peptide (25-35) $ED_{50}$ (μg/ml) HUVEC | Anti-βA peptide (1-42) $ED_{50}$ (μg/ml) HUVEC | Antioxidant $IC_{50}$ (μg/ml) |
|---|---|---|---|---|---|---|
| 1 | 7.0 | 10 | 6.0 | 12 | 13 | 28.2 |
| 2 | 4.0 | 5.0 | 4.0 | 4.5 | 5.0 | 36.2 |
| 3 | 2.0 | 3.5 | 2.5 | 2.4 | 2.0 | >200 |
| 4 | 0.5 | 1.0 | 1.2 | 0.8 | 1.0 | >200 |
| 5 | 2.5 | 3.0 | 1.5 | 2.0 | 1.5 | >200 |
| 6 | 1.0 | 2.0 | 1.0 | 1.5 | 1.0 | >200 |

EXAMPLE 3

Curcuminoid Analogue Synthesis

According to this example, curcuminoids and curcuminoid analogues were synthesized.

Figure 2:
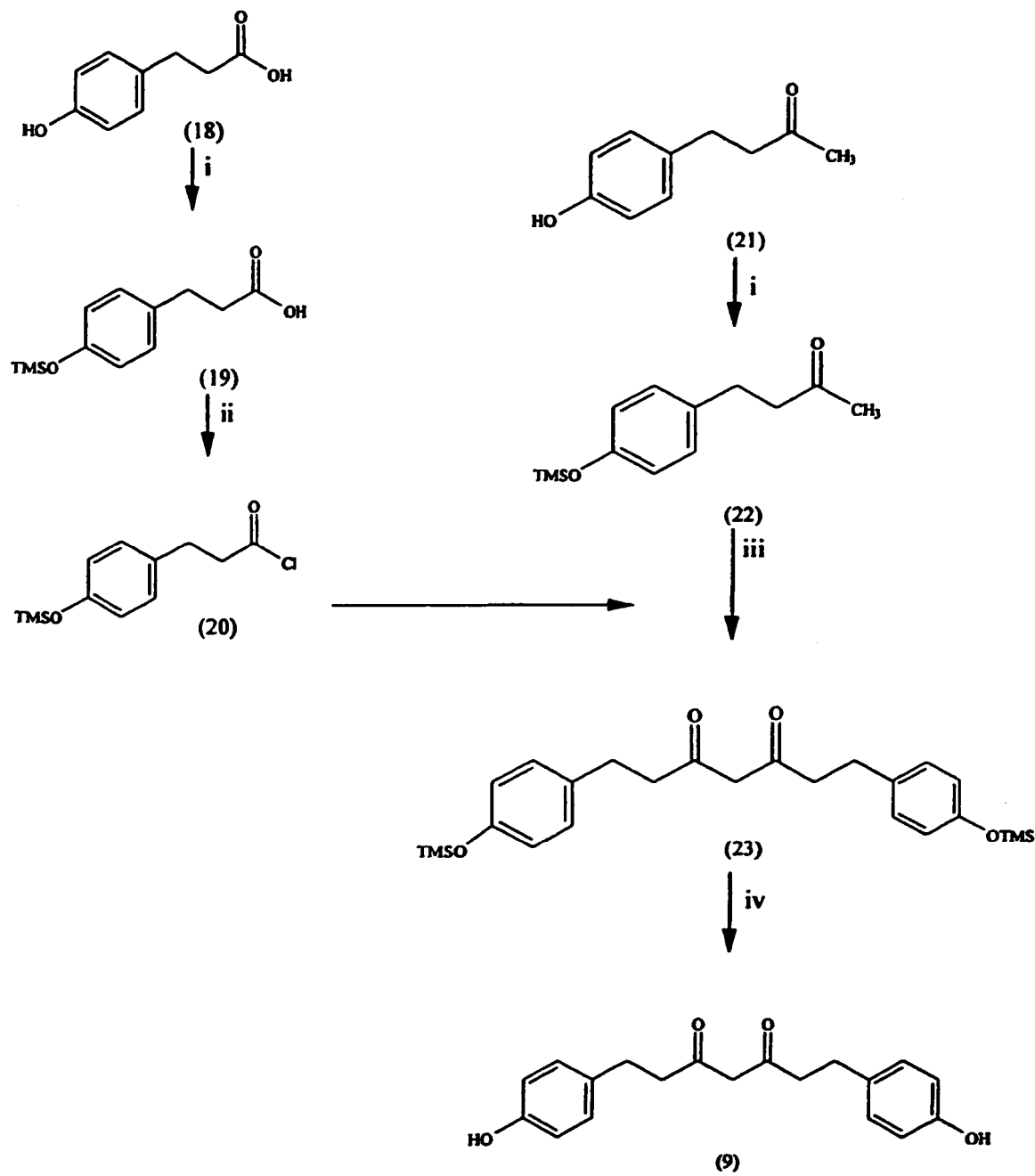
FIG. 2 shows a scheme for the synthesis of dihydro- and tetrahydro-curcuminoids.

Dihydro- and tetrahydro-curcuminpids were synthesized by the procedure illustrated in FIG. 2. 3-(4-hydroxyphenyl) propanoic acid, compound (18), was treated with TMSCl (1.3 equivalents) in the presence of 1.1 equivalents of triethylamine in $THF/CH_2Cl_2$ (50/50) solution to precipitate triethylammonium chloride as a white solid. The reaction was over within a few minutes, and only the phenolic position was protected. The white ammonium salt was filtered, and the filtrate was diluted with ethyl acetate. The resulting solution was washed with water three times, dried ($MgSO_4$), filtered, and the solvent was removed under vacuum to afford the TMS protected carboxylic acid, compound (19), in quantitative yield. The TMS protected carboxytic acid, compound (19), was converted to the corresponding acyl chloride, compound (20), by refluxing in oxalyl chloride for 30 min, and the remaining oxalyl chloride was removed under a stream of $N_2$ gas. 4-(4-hydroxyphenyl)-2-butanone, compound (21), was treated with TMSCl (1.3 equivalents) in the presence of triethylamine (1.1 equiv) in $CH_2Cl_2$, yielding the TMS protected product, compound (22). The ammonium chloride precipitate was filtered, and the filtrate was diluted with ethyl acetate. The resulting solution was washed with water (3×), dried ($MgSO_4$), filtered, and the solvent was removed under vacuum to afford compound (22), in quantitative yield. Compound (22) was treated with lithium diisopropylamide (LDA, 1.5 M in THF, 1. equiv) in tetrahydrofuran (THF) at −78° C. under $N_2$ for 20 min and 1.1 equivalents of the TMS protected acyl chloride, compound (20), dissolved in THF was added. The reaction mixture was stirred at −78° C. for 15 minutes and slowly warmed to room temperature. The reaction mixture was quenched with water and poured into ethyl acetate. The organic layer was washed three times with water and the water layer was back washed (2×) with ethyl acetate. The organic layers were combined, dried ($MgSO_4$), filtered, and the solvent was removed under vacuum. The residue was stirred in methanol in the presence of $K_2CO_3$ for 30 min to remove TMS protection. The solution was acidified with 2N HCl and poured into ethyl acetate. The aqueous layer was partitioned three times with ethyl acetate and the organic layers were combined, dried ($MgSO_4$), filtered, and the solvent was removed under vacuum. The residue was column chromatographed over silica gel using a gradient elution of ethyl acetate/petroleum ether to afford compound (9). Compound (9) was further purified using semi-preparative HPLC using an acetonitrile/water (90/10) solvent system to give pure synthesized curcuminoid compound (9) in 45% overall yield. Similarly, the unsymmetric synthesized curcuminoid compound (4) was prepared in 40% overall yield.

Figure 3:
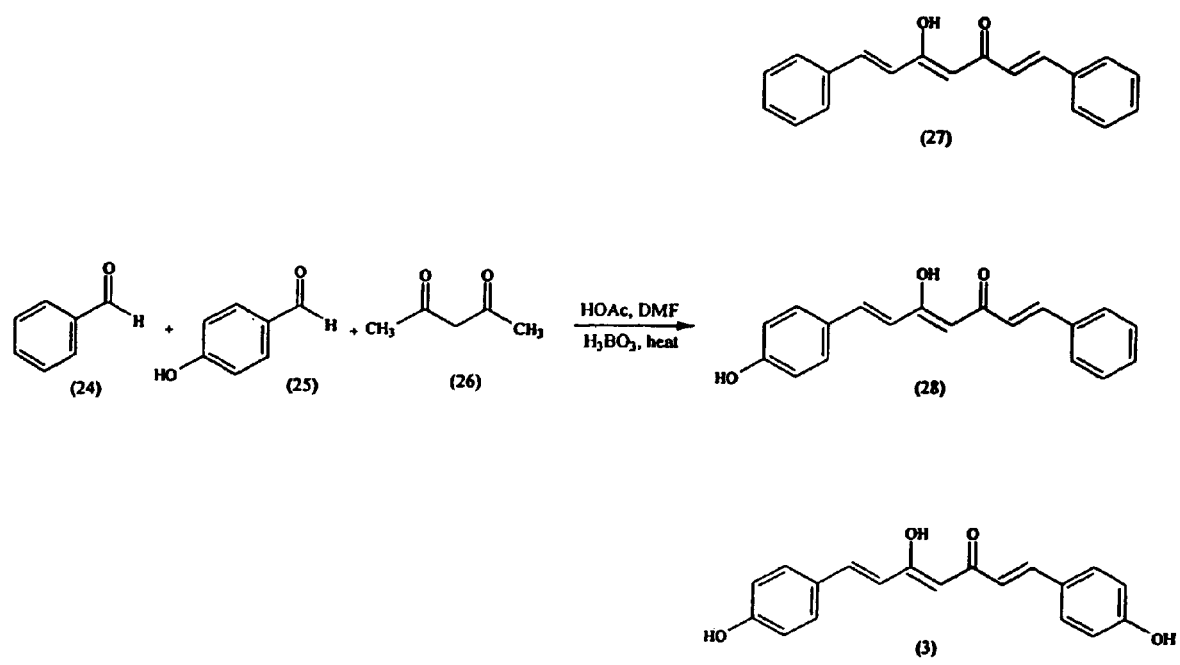
FIG. 3 shows a scheme for the synthesis of symmetric and unsymmetric curcumin analogues and related compounds.

Both symmetric and unsymmetric curcumin analogues and related compounds were prepared according to the procedure described in FIG. 3. Benzadehyde, compound (24), 4-hydroxybenzaldehyde, compound (25), 2,4-pentadione, compound (26), and boric acid were dissolved in dry N,N-dimethylformamide (DMF), and treated with a small amount of 1,2,3,4-tetrahydroquinoline and glacial acetic acid. This reaction yielded three products: a diphehyl group substituted product, compound (27), in 31% yield, a dihydroxyphenyl group substituted product, compound (3), in 6% yield, and a hydroxyphenyl phenyl substituted product, compound (28), in 11% yield. After working up the reaction, (ethyl acetate/water partitioning and back washing of the aqueous layer with ethyl acetate, followed by drying ($MgSO_4$) of the organic layer and removal of solvent in vacuo), the products were separated using semi-preparative HPLC (75% isopropyl alcohol/$H_2O$ eluent system). The physical data ($^1H$ NMR) of the dihydroxyphenyl product (3) was identical to that of the turmeric-derived natural product (3).

Figure 4:
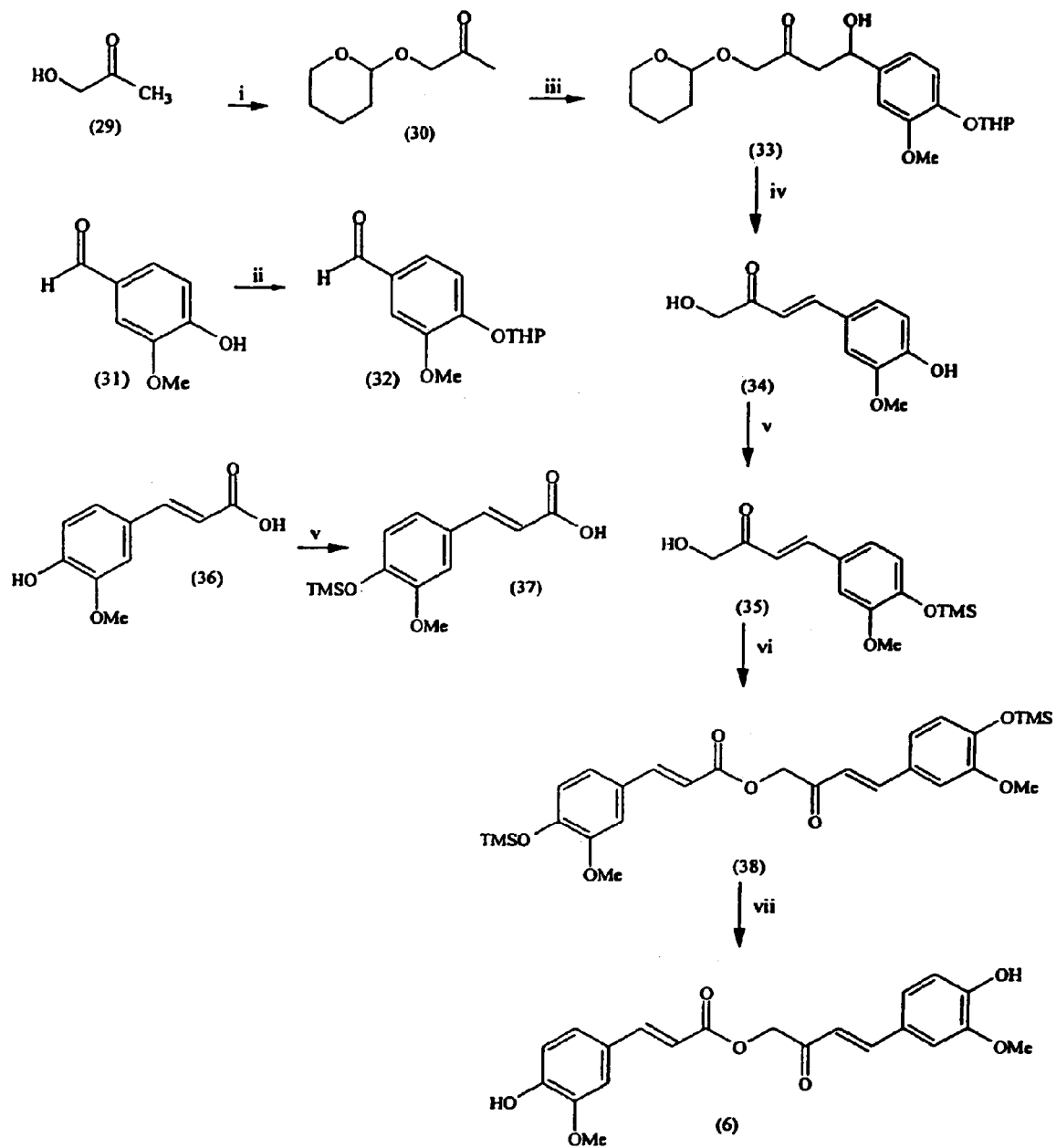
FIG. 4 shows a scheme for the synthesis of turmeric-derived natural product compound (6).

Natural product compound (6) was synthetically prepared according to the procedure shown in FIG. 4. The alcohol functionalities of acetol, compound (29), and vanillin, compound (31), were protected in quantitative yield as tetrahydropyran (THP) ethers using dihydropyran (DHP) in the presence of pyridinium para-toluene sulfonate (PPTS) in THF. The THP ether of acetol, compound (30), was reacted with LDA in THF at −78° C. and then reacted with the THP ether of vanillin, compound (32), to afford the β-hydroxy ketone, compound (33), in 73% yield. The THP ether was removed in the presence of PPTS, causing the dehydration of the β-hydroxyl group, and affording compound (34) in 72% yield. The phenolic group of compound (34) was selectively protected with a TMS group in quantitative yield to yield an alcohol, compound (35). The phenolic group of 4-hydroxy-3-methoxyphenyl propenoic acid, compound (36), was selectively protected with a TMS group in quantitative yield. The TMS protected carboxylic acid, compound (37), and the alcohol, compound (35), were coupled in the presence of dicyclohexylcarbodiimide (DCC) and dimethylamino-pyridine (DMAP) in THF at room temperature to afford 68% of the coupled product, compound (38). The TMS protecting groups of compound (38) were removed by stirring in a mixture of acetic acid/$H_2O$ in THF (1/1/5) to afford the desired product in 53% yield. Attempts to remove the TMS groups of compound (38) using tetran-butylammonium fluoride in THF resulted in the decomposition of the desired reaction product. The $^1$H NMR of the product was identical to that of turmeric-derived natural product compound (6).

EXAMPLE 4

Figure 5:
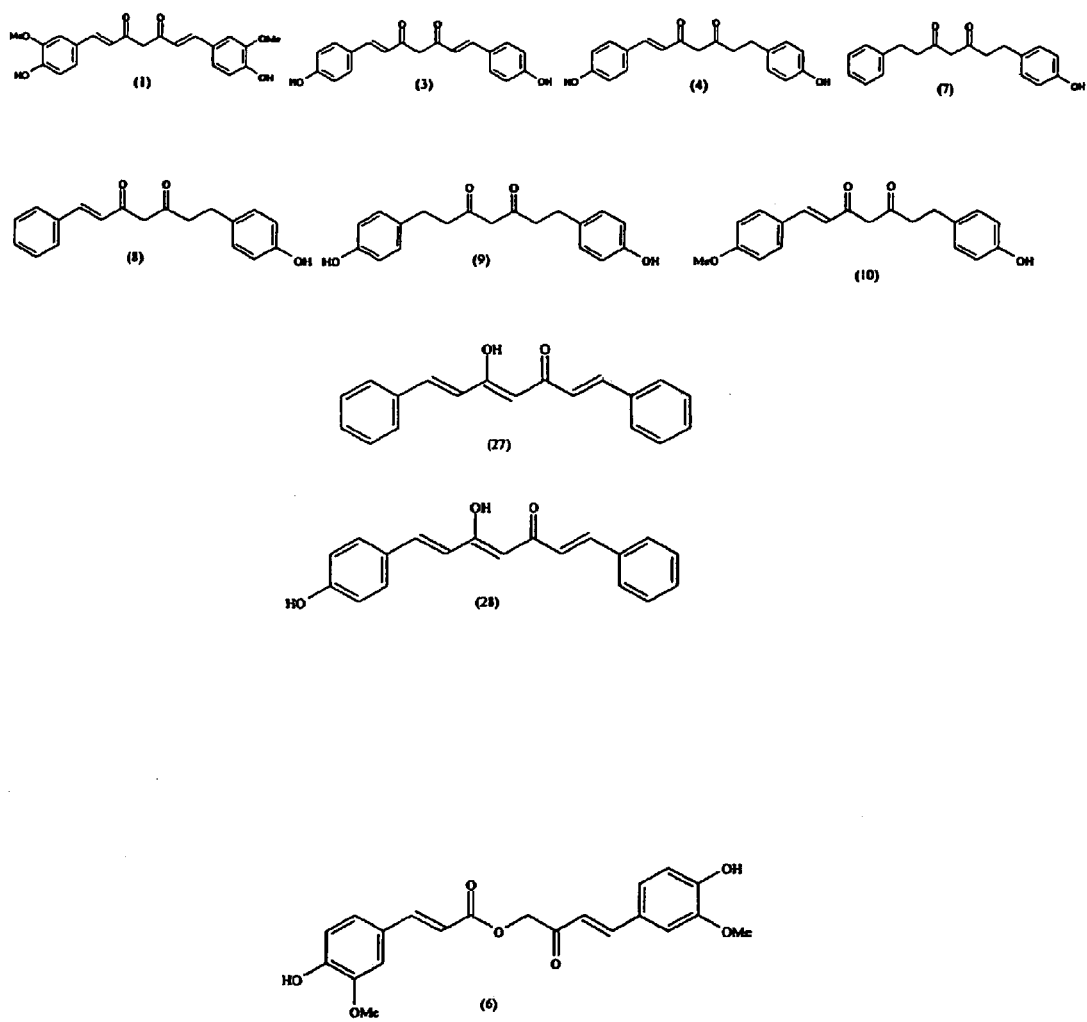
FIG. 5 shows the structures of curcuminoid conpounds that have been synthetically prepared and assayed for biological activity against βA peptide-induced toxicity.

Inhibitory Activity and Antioxidant Potency of Curcuminoid Synthetic Analogues Against Beta Amyloid-induced Toxicity According to this example, the inhibitory activity of the synthetic curcuminoid analogues against βA peptide-induced toxicity was measured by the MTT reduction assay described in example 1. Synthesized compounds (1), (3), (4), and (9) (shown in FIG. 5) protected the cells from βA peptide insult (Table 2). Microscopic analyses of βA peptide treated cells further including synthesized curcuminoid compounds (3) and (4) also demonstrated that these compounds effectively protect cells from βA peptide insults. The positive control and cells treated with compounds (3) and (4) maintained MIT formazan granules in the cytosole, a sign of viable cells, while the negative control showed extensive MTT formazan spike processes, a sign of nonviable cells. As was the case with the structurally analogous natural product compound, natural product compound (4), synthesized curcuminoid compound (4) provided the best protection. Interestingly, synthesized curcuminoid compounds (7), (8), and (10) were cytotoxic. Apparently, the presence of a hydroxyl group at the 4-position of phenyl ring or the size of substituent at that position is important for the expression of the desired biological activity. The results of the MTT assay were confirmed by the LDH methodology set forth in example 2. The synthesized curcuminoid compounds are shown in FIG. 5.

The ability of the synthesized curcuminoid compounds to scavenge DPPH free radicals was measured by observing the optical density change of the radicals at 515 nm in accordance with the antioxidant assay set forth in Example 2. The results show that only compounds 1 and 3 have significant antioxidant activity (Table 2).

TABLE 2

Inhibitory Activity of Synthesized Curcuminoids against βA Peptide-Induced Toxicity against PC12 and IMR32 Cells and Antioxidant Activity of the Compounds.

| Compound | Anti-βA peptide (25-35) ED$_{50}$ (μg/ml) PC12 | Anti-βA peptide (1-42) ED$_{50}$ (μg/ml) PC12 | Anti-βA peptide (25-35) ED$_{50}$ (μg/ml) IMR32 | Anti-βA peptide (1-42) ED$_{50}$ (μg/ml) IMR32 | Antioxidant IC$_{50}$ (μg/ml) |
|---|---|---|---|---|---|
| 1 | 5.5 | 6.0 | 6.0 | 6.0 | 28.5 |
| 3 | 3.0 | 4.5 | 3.0 | 3.5 | 32.6 |
| 4 | 0.5 | 1.0 | 1.5 | 2.0 | >200 |
| 7 | toxic | toxic | toxic | toxic | >200 |
| 8 | toxic | toxic | toxic | toxic | >200 |
| 9 | 10.0 | 9.0 | 12.0 | 11.0 | >200 |
| 10 | toxic | toxic | toxic | toxic | >200 |

EXAMPLE 5

Figure 6:
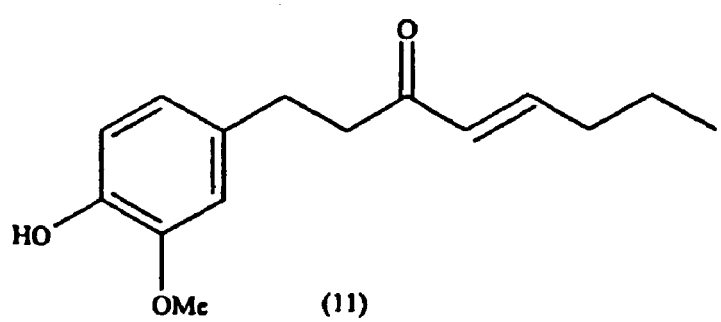
FIG. 6 shows the structures of ginger-derived natural product compounds that protected PC12, IMR32, and HUVEC cells from βA peptide-induced toxicity.
Figure 6:
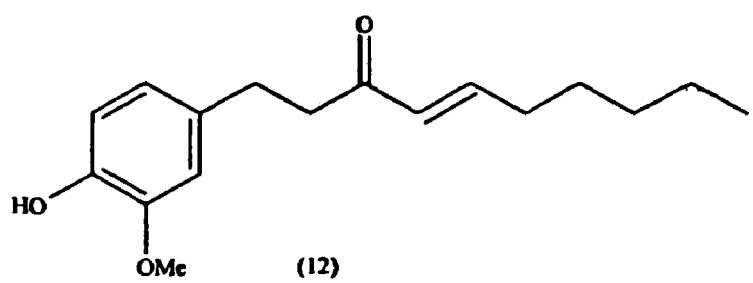
Figure 6:
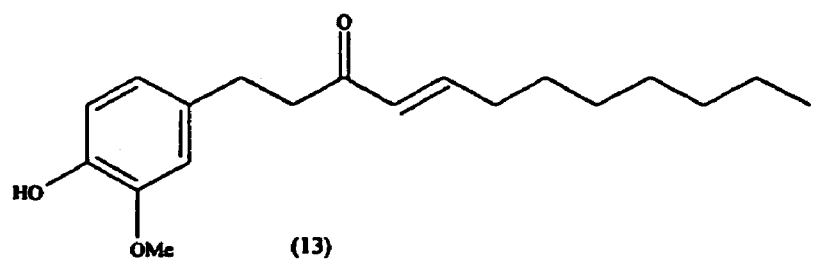
Figure 6:
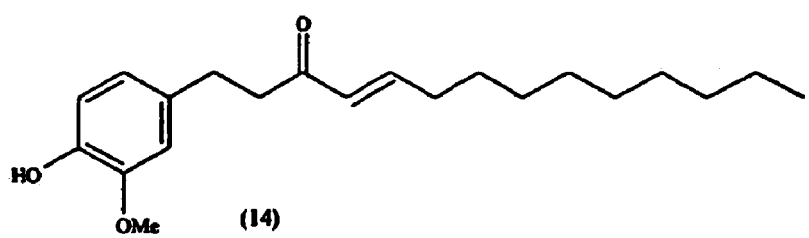

Isolation and Identification of Natural Product Compounds Derived from Ginger that Protect Cells from Beta Amyloid-induced Toxicity According to this example, natural product compounds that protect cells from βA peptide-induced toxicity were isolated from ginger by following bioassay-guided fractionation schemes. Briefly, ground ginger was extracted with 90% methanol overnight (2x), and the solvent was removed under vacuum at 35° C. The residue was partitioned between petroleum ether/water, dichloromethane/water, and ethyl acetate/water, successively. After removing the solvent under vacuum at 35° C., the residues from each partition were screened for inhibitory activity against βA peptide-induced cytotoxicity using PC12, IMR32, and HUVEC cells at 25, 5.0, and 1.0 μg/ml. The active principles were isolated from the residues of active fractions by a series of column chromatography using various resins (Amberchrom non-ionic resin and silica gel) and semi-preparative HPLC reverse-phased separation (isopropyl alcohol/water or acetonitrile/water solvent system). Four shogaols, natural product compounds (11), (12), (13), and (14) (shown in FIG. 6) were isolated from ginger, and their structures were elucidated using NMR (1-D and 2-D $^1$H, $^{13}$C, APT, HMBC) and mass spectrum analysis.

EXAMPLE 6

Inhibitory Activity of Ginger-derived Natural Product Compounds Against Beta Amyloid Toxicity According to this example, the inhibitory activity of natural product compounds (11), (12), (13), and (14) (shown in FIG. 6) against βA peptide-induced toxicity was measured by the MTT reduction assay set forth in example 1. These natural product compounds effectively protected PC12, IMR32, and HUVEC cells from βA peptide-induced toxicity (Table 2). The results of the MTT assay were confirmed by the LDH methodology set forth in example 2.

The ability of natural product compounds (11), (12), (13), and (14) to scavenge DPPH free radicals was measured by observing the optical density change of the radicals: at 515 nm in accordance with the antioxidant assay set forth in Example 2. None of these compounds exhibited significant antioxidant activity.

TABLE 3

Inhibitory Activity of Ginger-Derived Natural Product Compounds against βA Peptide-Induced Toxicity against PC12, IMR32, and HUVEC cells and Antioxidant Activity of the Compounds.

| Compound | Anti-βA peptide (25-35) ED$_{50}$ (μg/ml) PC12 | Anti-βA peptide (1-42) ED$_{50}$ (μg/ml) PC12 | Anti-βA peptide (25-35) ED$_{50}$ (μg/ml) IMR32 | Anti-βA peptide (25-35) ED$_{50}$ (μg/ml) HUVEC | Anti-βA peptide (1-42) ED$_{50}$ (μg/ml) HUVEC | Antioxidant IC$_{50}$ (μg/ml) |
|---|---|---|---|---|---|---|
| 11 | 15 | 12 | 15 | 20 | 20 | >200 |
| 12 | 9.0 | 10 | 8.0 | 20 | 18 | >200 |
| 13 | 3.0 | 4.0 | 2.0 | 8.0 | 8.0 | >200 |
| 14 | 2.0 | 2.0 | 1.5 | 4.0 | 5.0 | >200 |

EXAMPLE 7

Shogaol Analogue Synthesis

According to this example, shogaols and their analogues were successfully synthesized in 100 mg scale. Gingerols were synthesized from zingerone by conversion into the corresponding O-trimethylsilyl ether, deprotonation with lithium bis(trimethylsilyl)amide or lithium diisopropylamide (LDA), and regioselective aldol condensation. Shogaols are gingerol analogues with a 4,5-double bond, resulting from the elimination of the 5-hydroxy group.

Figure 7:
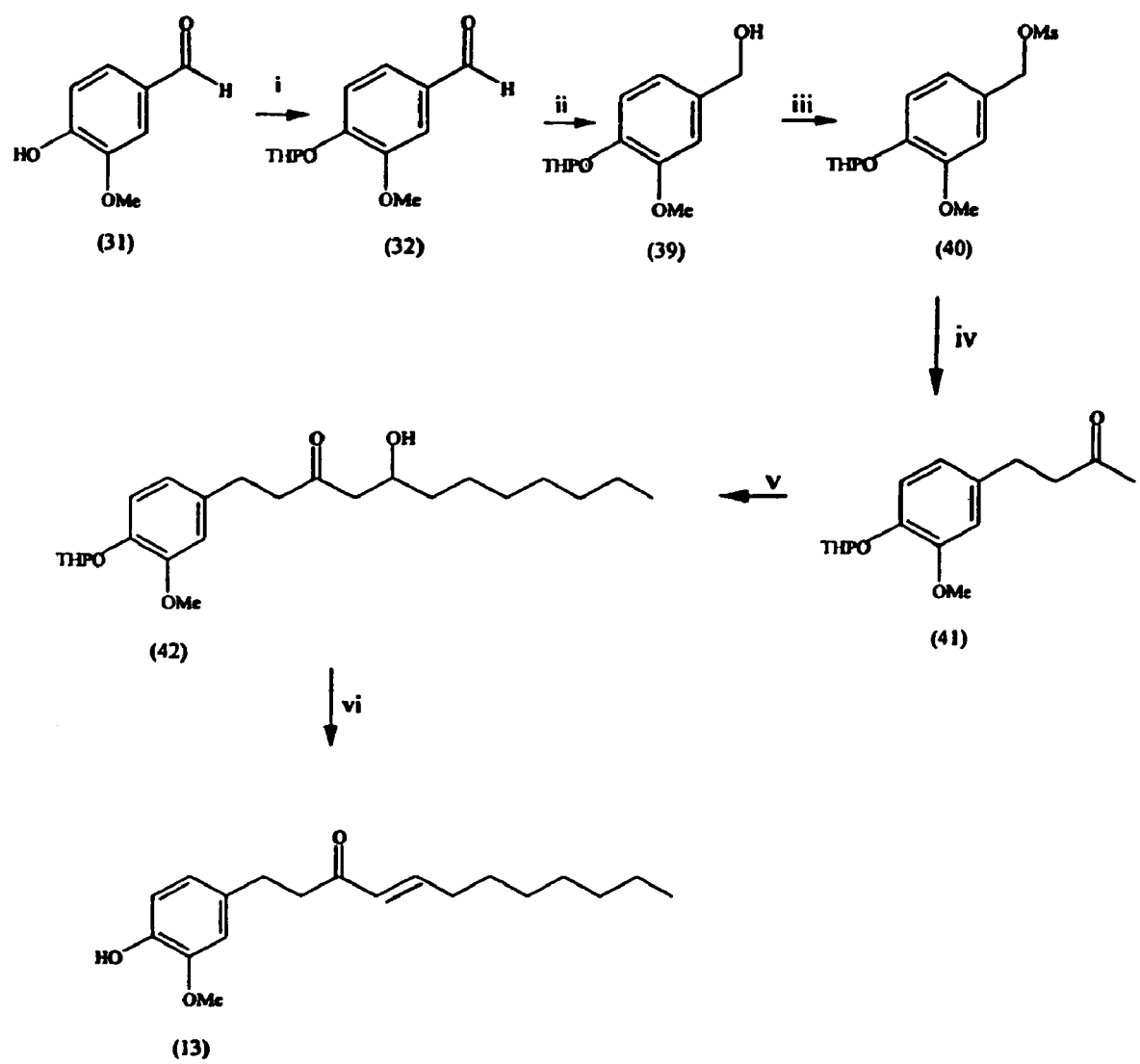
FIG. 7 shows a scheme for the synthesis of ginger-derived natural product compound (13).

The phenol group of vaniline, compound (31), was protected as the THP ether (DHP/PPTS/CH$_2$Cl$_2$) to yield compound (32), and the aldehyde group of compound (32) was reduced to the alcohol to yield compound (39) using $NaBH_4$ in THF as shown in FIG. 7. The resulting alcohol, compound (39), was mesylated (methanesulfonyl chloride/triethylamine/THF) and then reacted with in situ generated lithium acetonide (acetone/LDA/THF/−78° C.) at −78° C. under $N_2$ to yield compound (41). Compound (41) was reacted with LDA at −78° C. in THF under $N_2$ to generate lithium enolate which was then reacted with octyl aldehyde to afford the β-hydroxy ketone, compound (42). During treatment with PPTS in ethanol at 50° C. to remove the THP ether protecting group, dehydration occurred to afford [9]-shogaol, compound (13), which was identical to the ginger-derived natural product compound (13) (overall yield 37%).

Figure 8:
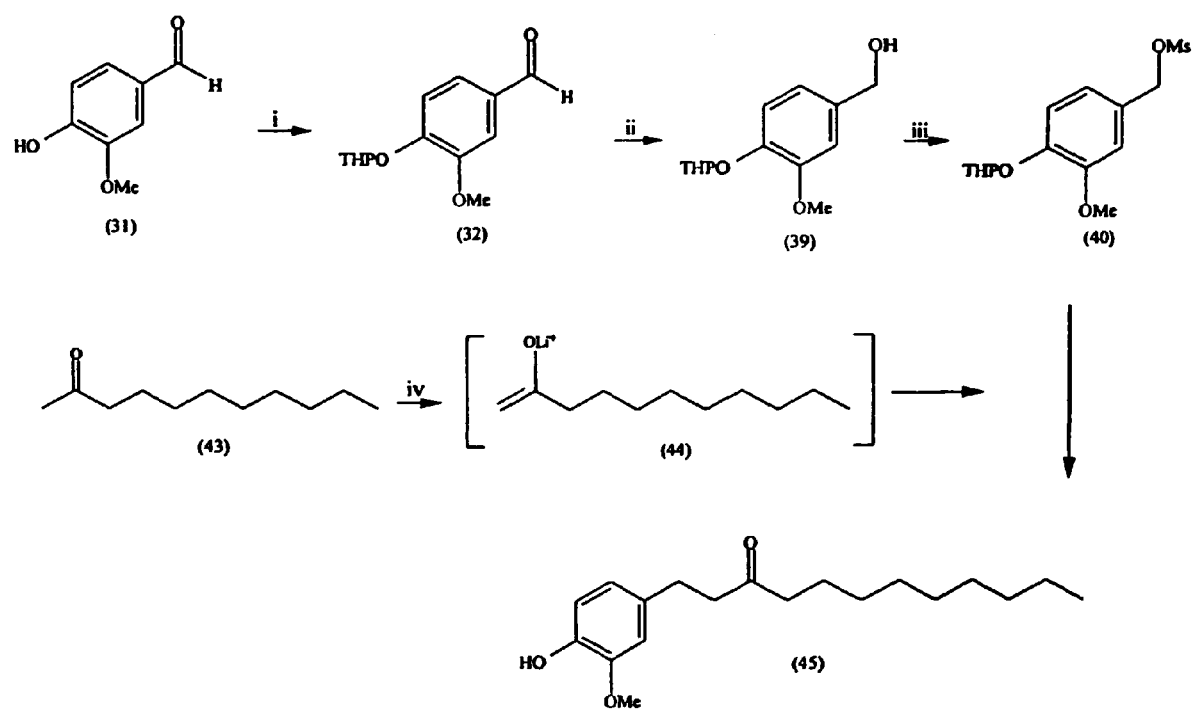
FIG. 8 shows a scheme for the synthesis of [9]-dihydroshogaol, compound (45).

The phenol group of vaniline, compound (31), was protected as the THP ether (DHP/PPTS/$CH_2Cl_2$) to yield compound (32), and the aldehyde group of compound (32) was reduced to the alcohol to yield compound (39) using $NaBH_4$ in THF as shown in FIG. 8. The resulting alcohol, compound (39), was mesylated (methanesulfonyl chloride/triethylamine/THF) and reacted with in situ generated lithium 2-undecanonide, compound (44), (2-undecanone/LDA/THF/−78° C.) at −78° C. under $N_2$. The THP ether protecting group was removed by farther treating the reaction mixture with PPTS in ethanol at 50° C. to afford [9]-dihydroshogaol, compound (45).

Figure 9:
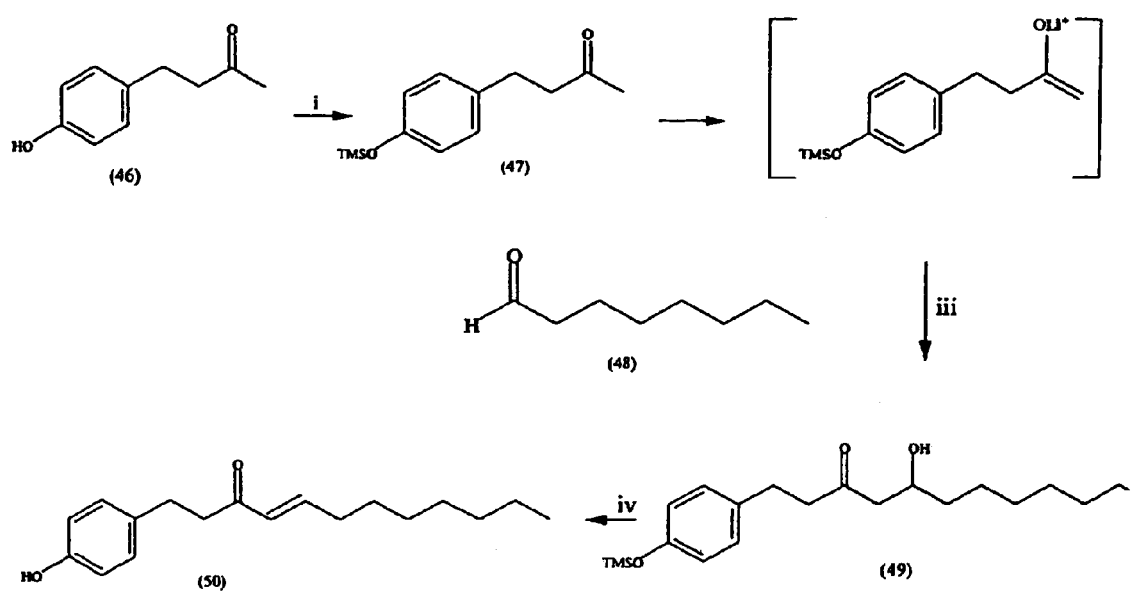
FIG. 9 shows a scheme for the synthesis of [9]-demothoxyshogaol, compound (50).

The phenol group on 4-(4-hydroxy-phenyl)-2-butanone, compound (46), was protected as the TMS ether (TMSCl/triethylamine/THF) at room temperature as shown in FIG. 9. The resulting ketone, compound (47), was reacted with LDA at −78° C. in THF under $N_2$ to generate lithium enolate which was reacted with octyl aldehyde compound (48), to afford the β-hydroxy ketone, compound (49). The TMS group was removed by stirring with $NaHCO_3$ in methanol at room temperature. Dehydration of the β-hydroxy group was achieved by further treatment of the reaction mixture with methanolic HCl (1 N) at room temperature to afford [9]-demethoxyshogaol, compound (50).

EXAMPLE 8

Figure 10:
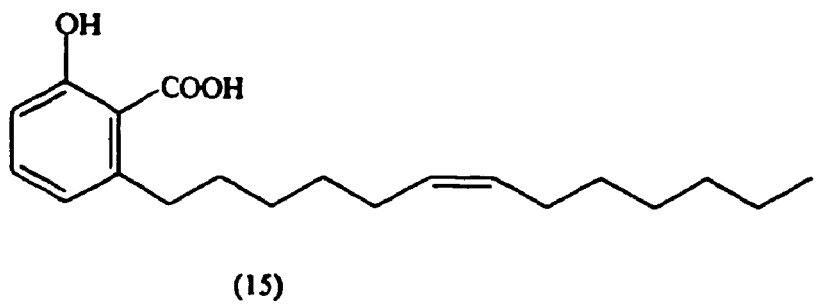
FIG. 10 shows the structures of *ginkgo biloba*-derived natural product compounds that protected PC12 and HUVEC cells from βA peptide-induced toxicity.
Figure 10:
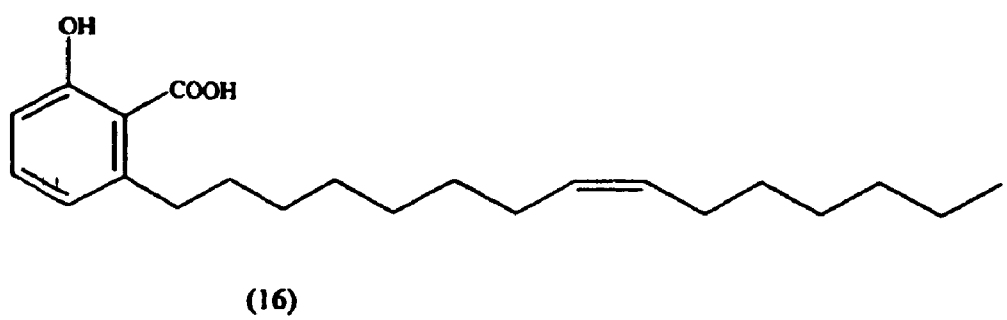

Isolation and Identification of Natural Product Compounds Derived from *Gingko Biloba* that Protect Cells from Beta Amyloid-induced Toxicity According to this example, freshly ground fresh ginkgo nuts (1 kg) were extracted with methanol (2×2000 ml) and sequentially partitioned with petroleum ether, ethyl acetate, dichloromethane, and butanol. The petroleum ether and ethyl acetate fractions protected PC12 and HUVEC cells from βA peptide(25-35)-induced cytotoxicity at $ED_{50}=10$ μg/ml. The active principles were isolated from the residues of active fractions by a series of column chromatography using various resins (Amberchrom non-ionic resin and silica gel) and semi-preparative HPLC reverse-phased separation (isopropyl alcohol/water or acelonitrile/water solvent system). The structures of the compounds were elucidated using 1-D and 2-D NMR techniques that include $^1H$, $^{13}C$, HMBC, and APT. Cis conformation of the double bond was unambiguously assigned in the $^1H$ NMR spectrum. The position of the double bond was elucidated by oxidatively cleaving it to acid functionality ($KMnO_4$ oxidation) and observing the mass spectral fragmentation pattern (EI 70 eV). The two compounds (15) and (16) have ginkgolic acid structures, and are shown in FIG. 10. These compounds have been previously isolated from ginkgo leaves, see Morimoto et al., *Chem. Pharm. Bull.* 16, 2282 (1968).

EXAMPLE 9

Inhibitory Activity of *Ginkgo Biloba*-Derived Natural Product Compounds Against Beta Amyloid Toxicity According to this example, the inhibitory activity of natural product compounds derived from *ginkgo biloba* against βA peptide-induced toxicity was measured by MTT reduction assay. The two *ginkgo biloba*-derived natural product compounds that do not possess antioxidant properties, compounds (15) and (16), were found to protect PC12, IMR32, and HUVEC cells from βA peptide-induced toxicity. The results of the MTT assay were confirmed by following the LDH methodology set forth in example 2. This example also provides data indicating that the ginkgolides A, B, and C, (−)bilobalide, and quercetin do not possess biological activity against βA peptide as had been postulated in the prior art.

TABLE 4

Inhibitory Activity of Ginkgolic Acids 1 and 2, Ginkgolide A, Ginkgolide B, Ginkgolide C, (−)-Bilobalide, and Quercetin Toward β-Insult Against PC12, IMR32, and HUVEC Cells.

| Compound | Anti-βA peptide (25-35) $ED_{50}$ (μg/mL) PC12 | Anti-βA peptide (1-42) $ED_{50}$ (μg/mL) PC12 | Anti-βA peptide (25-35) $ED_{50}$ (μg/mL) IMR32 | Anti-βA peptide (1-42) $ED_{50}$ (μg/mL) IMR32 | Anti-βA peptide (25-35) $ED_{50}$ (μg/mL) HUVEC | Anti-βA peptide (1-42) $ED_{50}$ (μg/mL) HUVEC |
|---|---|---|---|---|---|---|
| 15 | 3.0 | 2.0 | 3.5 | 2.5 | 5.0 | 1.5 |
| 16 | 2.0 | 1.0 | 2.0 | 1.0 | 2.5 | 1.0 |
| Ginkgolide A | toxic | toxic | toxic | toxic | toxic | toxic |
| Ginkgolide B | toxic | toxic | toxic | toxic | toxic | toxic |
| Ginkgolide C | toxic | toxic | toxic | toxic | toxic | toxic |
| (−)-Bilobalide | toxic | toxic | toxic | toxic | toxic | toxic |
| Quercetin | >20 | >20 | >20 | >20 | >20 | >20 |

EXAMPLE 10

A Proposed Gingkolic Acid Synthesis

Figure 11:
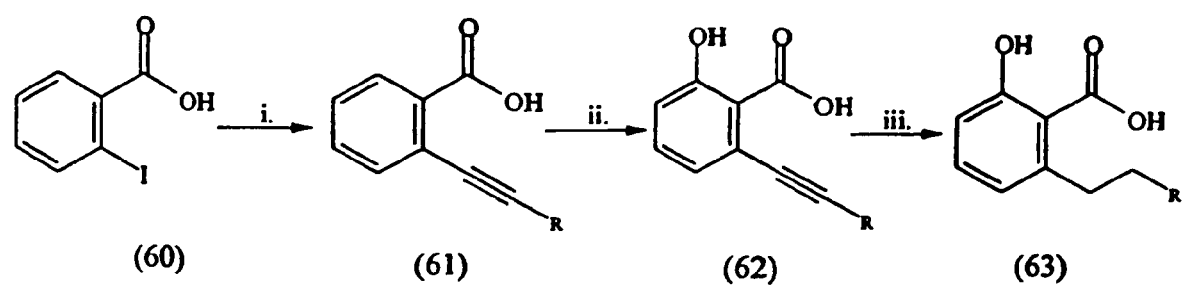
FIG. 11 shows a proposed synthesis for ginkolic acids and their analogues.

According to this example, a gingkolic acid synthesis is proposed as shown in FIG. 11. The benzoic acid, compound (60) and an alkyne having a terminal carbon-carbon triple bond, R, are treated with tetrakis(triphenylphosphine)palladium, in the presence of diisopropyl amine and copper(I) iodide to yield an alkyne substituted benzoic acid, compound (61). Compound (61) is treated with LDA in THF, the temperature is lowered to −78° C. and the reaction mixture is treated with oxodiperoxymolybdenum (pyridine)-(hexamethylphosphoric triamide) (MoOPh) to yield a hydroxy functionalized product, compound (62). Compound (62) is then reacted with hydrogen gas over a palladium/carbon catalyst, and treated with acetic acid to yield the desired ginkgolic acid product, compound (63).

EXAMPLE 11

Control Study

As a control study, vitamin A, β-carotene, vitamin C, and vitamin E were tested for both anti-βA peptide(25-35) and anti-βA peptide(1-42) activity. Since these vitamins are suggested for the delaying the onset of AD, the biological activity of the compounds of the invention were compared with these vitamins. Under the experimental conditions, these vitamins did not protect PC12 cells from βA peptide insults even at 200 μg/ml. Congo red was also tested because it has been reported to inhibit βA peptide fibril-induced toxicity against PC12 cells. At high concentrations of Congo red (>25 μg/ml), the data from the cell viability evaluation using MTT reduction assay was not reliable because of the dye's intense red color. Nevertheless, the natural product compounds (1), (2), (3), and (4) and natural product compounds (11), (12), (13), and (14) ($ED_{50}$=20.0-0.5 μg/ml) are more than 20-40 times as effective in protecting PC12 cells against βA peptide insults when compared with these vitamins and other agents.

EXAMPLE 12

Reduced Glulathione Assisted βA Peptide Toxicity Inhibition Assay

According to this example, the compounds of the invention were evaluated to ascertain if their antioxidant potency was increased when administered in conjunction with reduced glutathione. The synergistic interaction between estrogens and the intracellular antioxidant, reduced glutathione (GSH), was reported to protect neurons from βA peptide-induced toxicity. See Green et al., Proc. Natl. Acad. Sci. USA 73, 2424 (1976). The possible involvement of this mechanism was evaluated using PC12 cells with the compounds of the invention. The dose of GSH used in this study was comparable to the low micromolar GSH (3.25 μM) concentrations found in the cerebrospinal fluid and used by Green et al. It was hypothesized that if the compounds' of the invention ability to protect cells from βA peptide-induced toxicity resulted from the compounds' antioxidant potency, administration of a compound of the invention concurrently with GSH should improve the $ED_{50}$ and $IC_{50}$ values for the compounds. Under the experimental conditions, GSH did not influence the compounds' ability to protect cells from βA peptide insults, and did not enhance the antioxidant potency of the compounds.

EXAMPLE 13

Neurite Extension and F-actin Redistribution Assays

According to this example, the neurotrophic properties of the compounds of the invention were evaluated by monitoring the compounds' ability to induce neurite outgrowth from PC12 cells. PC12 cells (500 cells/ml) were plated on 6-well plates (Corning, New York, N.Y.) and incubated overnight before treatment with the compounds of the invention. Cells were incubated with a gradient of compound concentrations ranging from 50 ng/ml to 50 μg/ml. Neurite outgrowth of PC12 cells was monitored for 6 days with a culture media exchange every 3 days. As a control study, cells were also incubated with NGF (100 ng/ml) whose potential to induce neurite outgrowth in PC 12 cells is known.

An F-actin redistribution assay with Biotin-NGF was performed on PC12 cells according to a modified procedure for NGF-induced F-actin redistribution. See Paves et al., Exp. Cell Res. 186, 218 (1990). PC12 cells ($1.0 \times 10^4$ cells/ml) were plated on collagen-coated coverslips in 6-well plates (Corning, New York, N.Y.). After an overnight incubation in culture media, the cells were incubated with 19 nM of either Biotin-NGF or native NGF for 5 to 15 min. Control PC 12 cells were incubated without NGF. Prior to NGF treatment, another group of control cells was pre-incubated with cytochalasin D (10 μM; Sigma, St. Louis, Mo.) for 20 min to determine the involvement of F-actin treadmilling in F-actin redistribution, and to demonstrate the specificity of fluorescent staining with fluorescent phalloidin conjugates. The cells were fixed with 4% paraformaldehyde in PBS, pH 7.5, for 5 min, and permeabilized with 0.1% Triton X-100 in PBS for 10 min. Then, the cells were incubated with fluorescent phalloidin conjugates (1 μg/ml; Sigma, St. Louis, Mo.) for 30 min at 37° C. As a control study, some cells were not permeabilized with Triton X-100 to determine the levels of nonspecific staining of membrane-impermeable fluorescent phalloidin conjugates. In order to determine the levels of autofluorescence of PC12 cells, some cells were incubated without fluorescent phallidin conjugates. The distribution of fluorescent phalloidin conjugates was examined using a fluorescent microscope (Axiophot, Zeiss).

Compounds (4) and (6) were shown to promote neurite outgrowth in PC12 cells, and constitute the first plant-derived natural product compounds exhibiting a neurotrophic effect. Since the first report of NGF-induced neurite outgrowth from PC12 cells, see Greene et al., Proc. Nal. Acad. Sci. USA 73, 2424 (1976), the neurotrophic effects of various compounds have been represented by their potency to induce neurite outgrowth from PC12 cells. See Lazarovici et al., Adv. Exp. Med. Biol 391,367 (1996). The neurotrophic properties of compound (6) were further demonstrated by its ability to induce F-actin redistribution in PC12 cells.

A detailed microscopic analysis on the neurite outgrowth was carried out using compound (6) on PC12 cells. This effect was remarkably faster (overnight) than that of NGF which usually requires more than 24 hours for neurite generation. Interestingly, compound (6) caused a remarkable enhancement of the neurite outgrowth in the presence of NGF, suggesting that compound (6) and NGF complement each other in the neurite outgrowth process. In addition, compound (6) appears to cause more complete neuronal differentiation. Compound (6) and NGF treatment over 6 days caused neurite outgrowth to 1,500 μm in length.

The appearance of membrane ruffling accompanied by the rapid redistribution of F-actin has been shown to be closely related to the subsequent outgrowth of neurites. Compound (6) also induced rapid redistribution of F-actin with noticeable cell spreading within a few minutes of addition in PC12 cells. Compound (6) appears to enhance the neurotrophic effect of NGF by assisting NGF-induced F-actin redistribution. Since NGF has been known to inhibit the cytotoxicity of βA peptide, it is hypothesized that the anti-βA peptide activity of this compound is closely related to its neurotrophic properties.

The effects of NGF on the distribution of F-actin were examined in PC12 cells. F-actin appeared to be diffusely distributed in undifferentiated cells, and minute F-actin positive filopodia were observed along the sites of cell-substrate adhesion. Within 5 to 15 min. after the addition of NGF, changes in the distribution of F-actin were observed. One of the changes induced by NGF was the appearance of a continuous radial distribution of F-actin, known as F-actin positive filopodia, in accordance with the increased adhesion properties of the cells. For quantitation of PC12 cells with F-actin positive filopodia, 300 substratum-attached PC12 cells were counted from each group of cells incubated with NGF or without NGF. Cells with a continuous radial F-actin filament along at least ⅓ of the cell edge were counted as redistributed F-actin positive. When cells were incubated with NGF, about 36-38% of cells were observed with F-actin positive filopodia. The experiment without NGF treatment showed that only about 8% of cells appeared with F-actin positive filopodia However, the morphology of the filopodia was distinctively different between the cells incubated with or without NGF. In a control experiment, PC12 cells without incubation with either phalloidin or Triton X-1000 did not show any specific staining. PC12 cells pre-incubated with cytochalasin D prior to NGF treatment showed a granular distribution of F-actin instead of showing NGF-induced F-actin positive filopodia.

EXAMPLE 14

Determination of Ability of Compounds of the Invention to Pass Through the Blood Brain Barrier According to this example, the ability of the compounds of the invention to pass through the blood brain barrier was measured. The ability of comounds to cross the blood brain barrier is represented by the log of the partition coefficient (P) of a molecule of the invention between water and octane alcohol. Natural product compounds (1) and (3) were found to have log P values of 3.4 and 3.1, respectively. Accordingly, the octane alcohol fraction contained more than 1000 times as much of the compounds as the water fraction. These results suggest that the compounds are able to cross the blood brain barrier.

Although the present invention has been described in considerable detail with reference to certain preferred embodiments thereof, other versions are possible. Therefore, the spirt and scope of the appended claims should not be limited to the preferred embodiments contained herein.

What is claimed is:

1. A method for the treatment of beta-Amyloid protein-induced cytotoxicity in a human brain comprising administering to a subject suffering from the beta-Amyloid protein-induced disease a therapeutically effective amount of a compound having the formula (V):

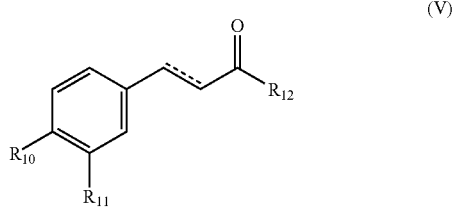

(V)

or a pharmaceutically acceptable salt or ester thereof, wherein:

the dotted configuration . . . is optionally a single bond or a double bond;

$R_{10}$ is selected from the group consisting of OH, OMe, OR', and X wherein R' is alkyl, alkenyl, or alkynyl, and X is F, Cl, Br, or I;

$R_{11}$ is selected from the group consisting of H, OH, OMe, and OR' wherein R' is alkyl, alkenyl, or alkynyl; and $R_{12}$ is selected from the group consisting of alkyl, alkenyl, and alkynyl.

2. The method according to claim 1 wherein:

$R_{10}$ is selected from the group consisting of OH, OMe, OR", and X wherein R" is $(CH_2)_n CH_3$ and n is 1-7, and X is F, Cl, Br, or I;

$R_{11}$ is selected from the group consisting of H, OH, OMe, and OR" wherein R" is $(CH_2)_n CH_3$ and n is 1-7; and $R_{12}$ is selected from the group consisting of

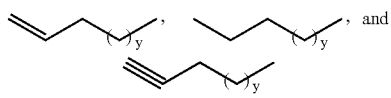

and y is 1-9.

3. The method according to claim 1 wherein:

the dotted configuration represents a single bond;

$R_{10}$ is OH;

$R_{11}$ is selected from the group consisting of H and OMe; and $R_{12}$ is selected from the group consisting of

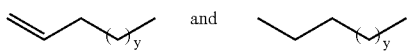

and y is 1-9.

4. The method according to claim 1 wherein the subject is suffering from Alzheimer's disease.

5. The method according to claim 1 in which the beta-amyloid protein-induced cytotoxicity is neurotoxicity.

6. The method according to claim 1 wherein a purified and isolated compound selected from the group consisting of formula (V) is administered.

* * * * *